United States Patent [19]

Bortinger et al.

[11] Patent Number: 4,851,605
[45] Date of Patent: Jul. 25, 1989

[54] PROCESS FOR SYNTHESIZING A ZEOLITE CATALYST ON A PH CONTROLLED SODIUM FREE BASIS

[75] Inventors: Arie Bortinger, Ridgewood; Wim Pieters, Morristown; Elena N. Suciu, Ridgewood, all of N.J.

[73] Assignee: Exxon Research & Engineering Co., Florham Park, N.J.

[21] Appl. No.: 630,723

[22] Filed: Jul. 13, 1984

[51] Int. Cl.$^4$ .............................................. C07C 1/20
[52] U.S. Cl. .................................. 585/640; 585/639; 423/328; 423/329
[58] Field of Search ............................. 585/639, 640; 423/328 T, 329 T

[56] References Cited

U.S. PATENT DOCUMENTS

| | | | |
|---|---|---|---|
| 4,377,502 | 3/1983 | Klotz | 423/329 T |
| 4,401,637 | 8/1983 | Marosi et al. | 423/329 T |
| 4,404,175 | 9/1983 | Marosi et al. | 423/329 T |
| 4,456,582 | 6/1984 | Marosi et al. | 423/329 T |
| 4,481,173 | 11/1984 | Chu | 423/329 T |
| 4,495,166 | 1/1985 | Calvert et al. | 423/329 T |

FOREIGN PATENT DOCUMENTS

| | | | |
|---|---|---|---|
| 0093519 | 9/1983 | European Pat. Off. | |
| 1581513 | 12/1980 | United Kingdom | 423/328 T |
| 2077709 | 12/1981 | United Kingdom | 423/328 T |

OTHER PUBLICATIONS

D. M. Bibby et al., "$NH_4^+$-Tetraalkyl Ammonium Systems in the Synthesis of Zeolites", Nature, vol. 285, (May 1980), pp. 30-31.

E. Kikuchi et al., "Preparation of Zeolite Catalyst for Synthesis of Lower Olefins from Methanol", J. Japan Petrol. Inst. 24(5), 275-280, (1981).

Z. Gabelica et al., "Synthesis and Characterization of ZSM-5 Type Zeolites", Applied Catalysis, 5, (1983), 227-248.

K. Chao et al., "Kinetic Studies on the Formation of Zeolite ZSM-5", J. Chem. Soc., Faraday Trans. 1, 1981, 77, 547-555.

A. Nastro et al., "Growth of Larger Crystals of ZSM-5 in the System $4(TPA)_2O-38(NH_4)_2O-x(Li, Na K)_2O-Al_2O_3-59SiO_2-75OH_2O$", Zeolites, 1983, vol. 3, Jan.

H. Nakamoto et al., "Crystallization of Zeolite ZSM-5 from Single Cation System", Chemistry Letters, pp. 1739-1742, 1981.

Synthesis and Growth of Zeolite ($NH_4$,TPA)-ZSM-5; N. Ghamami & L. Sand; Zeolites, vol. 3, pp. 155-162, (Apr. 1983).

Primary Examiner—Asok Pal
Attorney, Agent, or Firm—S. H. Markowitz; T. B. Morris

[57] ABSTRACT

A process for preparing a zeolite, e.g. ZSM-5, under controlled conditions of pH adjustment with an acid; $SiO_2/Al_2O_3$ mole ratio, and in the substantial absence of alkali metal cations, is disclosed, as well as a process for using the same to synthesize olefins from methanol and/or dimethyl ether.

12 Claims, 27 Drawing Sheets

PROCESS FOR SYNTHESIZING A ZEOLITE CATALYST ON A PH CONTROLLED SODIUM FREE BASIS

BACKGROUND OF THE INVENTION

This invention relates to methods of preparing shape selective zeolite catalysts, such as ZSM-5, and methods for their use to synthesize hydrocarbons such as olefins, in particular by conversion of lower monohydric alcohols and/or their ether derivatives.

Olefins, especially ethylene and propylene, are used on a large scale as intermediates for the manufacture of staple products such as olefin polymers, ethylene oxide, non-ionic detergents, glycols and fibre-forming polyesters. Processes for producing olefins usually involve non-catalytic pyrolysis of valatile hydrocarbons such as natural gas liquids or petroleum distillates. Catalytic pyrolysis processes have been proposed but do not appear to have reached industrial use.

In countries where such volatile hydrocarbons are not accessible but such feedstocks as coal, oil shale and methane, and consequently carbon monoxide/hydrogen synthesis gas derived therefrom, are available, it would be desirable to produce olefins from synthesis gas. It has been proposed to do this by converting the synthesis gas to methanol or to hydrocarbons and/or their oxygenated derivatives and reacting such products over shape selective acidic zeolites, e.g., of the ZSM-5 family. (See for example U.S. Pat. Nos. 3,894,106; 3,894,107; 4,025,571; and 4,052,479).

Shape selective zeolite materials, both natural and synthetic, have been demonstrated in the past to have catalytic capabilities for various types of organic compound conversions. These materials are ordered porous crystalline metalosilicates (e.g. aluminosilicates) having a definite crystalline structure within which there are a large number of cavities and channels, which are precisely uniform in size. Since the dimensions of these pores are such as to accept, for adsorption, molecules of certain dimensions while rejecting those of larger dimensions, these materials are deemed to possess the property of shape selectivity, have been referred to as "molecular sieves", and are utilized in a variety of ways to take advantage of these properties.

Such shape selective zeolites include a wide variety of positive ion-containing crystalline alumino-silicates, both natural and synthetic. Aluminosilicates can be described as a rigid three-dimensional network of $SiO_4$ and $AlO_4$ in which the tetrahedra are cross-linked by the sharing of oxygen atoms whereby the ratio of the total aluminum and silicon atoms to oxygen in 1:2. The electro-valence of the tetrahedra-containing aluminum is typically balanced by the inclusion in the crystal of a cation, for example an alkali metal or an alkaline earth metal cation. This can be expressed by formula wherein the ratio of Al to the number of various cations, such as Ca/2, Sr/2, Na, K, or Li is equal to unity. One type of cation may be exchanged either in entirety or partially by another type of cation utilizing ion exchange techniques in a conventional manner. By means of such cation exchange, it has been possible to vary the size of the pores in a given aluminosilicate by suitable selection of the particular cation. The spaces between the tetradehra are occupied by molecules of water prior to dehydration.

A preferred group of shape selective crystalline aluminosilicates, designated as those of the ZSM-5 type (e.g. see U.S. Pat. No. 3,702,886) is well known for use in the synthesis of olefins from syn gas derived materials such as methanol. Other shape selective zeolite materials are also well known for this purpose as discussed in the aforedescribed patents.

Unfortunately, the use of shape selective zeolites to catalyze methanol and/or dimehyl ether conversion for olefin production is not entirely satisfactory because such zeolites are also well known to catalyze the formation higher hydrocarbons from the initially produced olefins such as $C_{5+}$ paraffins, naphthenes, aromatics and alkylated aromatics. The particular distribution of products obtained from the use of any given catalyst is typically controlled by the reaction conditions, particularly temperature. Thus, where there is not a clear line of demarcation in product distribution as a function of temperature, it has been recognized (for example see U.S. Pat. No. 3,894,107) that as the reaction temperature is increased, the methanol conversion can be shifted in favor of the formation of ethers, olefins, aromatics and alkylated aromatics at respectively higher reaction temperatures. The use of temperature control to influence product distribution is illustrated in U.S. Pat. Nos. 4,052,429 and 4,058,576 wherein staging of the reactions is employed. The partial pressure of the reactant feed has also been observed to influence olefin selectivity. Thus, U.S. Pat. No. 4,025,576 discloses the use of a sub-atmospheric partial pressure of the reactant feed to improve its conversion with enhanced olefin selectivity. Subatmospheric partial pressure of the reactant feed is obtained either by maintaining a partial vaccuum in the conversion zone, or by co-feeding a diluent. Suitable diluents include any substantially inert substance that is a gas or vapor at reaction temperature such as steam, as well as nitrogen, carbon dioxide, carbon monoxide, hydrogen, and the like. When such diluents are used, total pressure in the reaction zone may range from subatmospheric up to about 1500 psia depending on the amount of diluent introduced with the feed. The diluent serves to assist in removing the heat of reaction generated in the more exothermic alcohol or ether conversions.

While optimization of operating conditions for a given zeolite to optimize a desired product distribution is important, such procedures are limited in the effects which can be produced thereby by inherent limitations in the physical and chemical properties of the zeolite.

Zeolite catalytic properties can be strongly influenced by such factors as crystal morphology, uniformity of crystal morphology, acidity characteristics and silica/alumina mole ratio, cation identity, pore size distribution, degree of crystallinity, as well as by control of numerous process conditions employed during the preparation of the zeolite which in turn can affect one or more of the aforedescribed characteristics in addition to producing indeterminate effects. Thus, the number of permutations and combinations of possible preparative process conditions, and resulting catalyst characteristics, is astronomical. Consequently, one is faced with a sea of variables in attempting to correlate a particular set of catalyst properties, a means for consistently achieving these properties, and the ultimate effect of a given set of properties on catalyst performance.

Furthermore, it will be understood that catalyst performance includes not only catalyst activity, and selectivity to a particular product distribution but also catalyst life.

For example, olefin synthesis reactions inevitably are accompanied by complex side reactions such as aromatization, polymerization, alkylation and the like to varying degrees. As a result of these complex reactions, a carbonaceous deposit is laid down on the catalyst which is referred to by petroleum engineers as "coke". The deposit of coke on the catalyst tends to seriously impair the catalyst efficiency for the principal reaction desired, and to substantially decrease the rate of conversion and/or the selectivity of the process. Thus, it is common to remove the catalyst from the reaction zone after coke has been deposited thereon and to regenerate it by burning the coke in a stream of oxidizing gas. The regenerated catalyst is returned to the conversion stage of the process cycle. The period of use between catalyst regenerations is often referred to as catalyst life. In short, coke deposits are believed to be a primary contributing factor to reductions in catalyst life. There are obvious economic incentives to improve the catalyst life such as the savings in capital investment for regeneration equipment.

As with such catalyst properties as activity and selectivity, one can control catalyst life through control of the operating conditions. However, it would be a significant advantage if catalyst life could be improved by improving the nature of the catalyst itself through its preparative procedure.

Unfortunately, it is very difficult to predict improvements in catalyst performance from variations in conventional methods of synthesis. This stems from the fact that the most conventional way to identify a particular zeolite is by its characteristic X-ray diffraction pattern. However, catalyst performance of two zeolites with the same XRD pattern can differ drastically, in many instances for indeterminative reasons. One is therefore forced to search beyond the XRD pattern of a zeolite capable of enhancing catalyst performance.

The present invention focuses on the combination of pH control with the use of a metal, e.g., sodium, free system at specifically defined $SiO_2/Al_2O_3$ mole ratio conducive to the synthesis of olefins from methanol.

Regarding the use of a sodium free system, it was alleged in Barrer et al, U.S. Pat. No. 3,306,922, that they were the first to prepare crystalline zeolites containing a substantial weight percent of a cation other than sodium or other metal cation, namely, a tetra lower alkyl ammonium cation in the form of a hydroxide. The zeolites prepared in this manner are limited to the A, X, Y, and B types which all appear to possess $SiO_2:Al_2O_3$ mole ratios of not greater than about 10. It was observed by Barrer et al that the electrovalent balance within the framework of silica and alumina tetrahedra during the zeolite synthesis was thought at the time of their invention to be only attainable by having a substantial quantity of metal cations, such as sodium present in the reaction mixture. Typically, when a metal cation had been included in the reactant mixture and the synthesis reaction completed, the metal ions which occupied the cationic sites of the crystal were then optionally replaced by a wide variety of other metallic cations using ion exchange techniques.

However, Barrer et al do acknowledge at Col. 4, Lines 22 et seq, that small quantities of alkali metal cations in the reaction mixture are beneficial for reducing the preparation time of the zeolite. The zeolites disclosed in Barrer et al are employed as molecular sieve adsorbents with no mention of catalytic activity.

One advantage of eliminating the presence of alkali and alkaline earth metal cations from the reaction mixture in which zeolite crystallization is conducted, is the elimination of an exchange step to remove or replace such metal cations from the zeolite crystal structure if such exchange is contemplated for the end use of the zeolite.

The basic ZSM-5 patent, namely, U.S. Pat. No. 3,702,886 discloses a binary metal-organic cation system wherein crystallization occurs from reaction mixtures containing alkali or alkaline earth metal cations (typically Na and tetrapropyl ammonium ($TPA^+$)) cations. Where the metal cation is sodium it is typically derived from sodium hydroxide and/or sodium silicate. The tetrapropyl ammonium cation is typically derived from the hydroxide or bromide salt thereof.

British Patent Specification No. 1,581,513 discloses a method for preparing zeolites having the same structure as ZSM-5 using a mono-organic cation based system free of sodium. The organic cation can be tetramethyl ammonium ($TMA^+$) or tetrapropyl ammonium ($TPA^+$). The $SiO_2/Al_2O_3$ mole ratio present in the initial reaction mixture can vary from 10 to 1000 with the ratio in the final zeolite being from 10 to 3000. The process of this patent is said to be also applicable to ZSM-12. When both $TMA^+$ and $TPA^+$ are present, many syntheses are said to yield a product of unusually large crystal size. Zeolites prepared in accordance with this patent are disclosed as being suitable for use as adsorbents or as catalysts for hydrogenation-dehydrogenation (p. 4, line 15), the production of gasoline boiling range hydrocarbon products from a "variety of feedstocks" which are left unspecified (p. 4, line 38), hydrocracking, reforming, hydroisomerization of normal paraffins, olefin isomerization, and desulfurization (p. 5). The use of these catalysts for the synthesis of olefins from methanol is not disclosed. Since the performance of catalyst prepared by this process is not disclosed for any of the suitable reactions, it is unclear what advantage is conferred by practice of the process. The elimination of an exchange step does not appear to be a factor since subsequent exchange steps are contemplated (p. 4, lines 55 et seq). The possibility of coke reduction is suggested for "many experiments" (p. 2, line 42) without identification as to which environments this statement applies. Thus, there appears to be no recognized relationship established between the process steps employed and the impact of these process steps on ultimate catalyst performance.

Furthermore, in contrast to British Patent Specification No. 1,581,513, it is reported in an article "Ammonium-tetraalkyl Ammonium Systems in The Synthesis of Zeolites", by D. Bibby, D. Milestone and P. Aldridge, Nature. Vol. 285, pp. 30-1 (1980) (hereinafter Bibby et al) that the authors had no success in preparing zeolites in the presence of tetraalkyl ammonium ($TAA^+$) cations only, but were successful in making ZSM-5 type zeolites in the presence of a binary cation system of $NH_4^+/TAA^+$ on a sodium free basis. The initial $SiO_2/Al_2O_3$ mole ratio employed in the reaction mixture, however, was calculated to be only about 319. Bibby et al have also commented that crystalline aluminum free analogous of ZSM-5, often called silicalite, could be prepared from a TAA-monocation system, but that the reaction proceeds slowly. The performance of catalysts prepared by the $NH_4^+/TAA^+$ system is not reported, although the authors have stated that the H- form of ZSM-5 produced by exchange of Na ions has potential for the conversion of oxygen-containing organic compounds, such as methylalcohol to hydrocarbons.

In the article "Crystallization of Zeolite ZSM-5 From a Single Cation System", by H. Nakamoto, and H. Takahashi, Chemical Letters, pp. 1739-1742 (1981), the authors report the production of a ZSM-5 zeolite in the presence of $TPA^+$ as the only cation, by control of the concentration ratios of $(TPA)_2O/SiO_2$, $SiO_2/Al_2O_3$, and $H_2O/SiO_2$ in the reaction mixture. They conclude that the crystallization rate is strongly dependent on the $(TPA)_2O/SiO_2$ mole ratio and indicate that a minimum ratio of 0.2 is necessary for the formation of ZSM-5 in their system (e.g. $SiO_2/Al_2O_3=100$; Temp.$=150°$ C.; $H_2O/SiO_2=81$; $Na/SiO_2=0.0038$), thereby ensuring sufficient alkalinity in the reaction mixture to induce dissolution of the amorphous solid to form soluble active species from which nuclei grow. Since crystallization was observed to occur rapidly after the induction period for dissolution, the formation of nuclei is suggested as the rate determining step in the overall process. No crystalline phase is observed after 5 days at a $(TPA)_2O/SiO_2$ ratio of 0.1. Increasing the $SiO_2/Al_2O_3$ ratio increased crystallization independent of whether single $TPA^+$ or binary $Na^+/TPA^+$ system is employed. However at $SiO_2/Al_2O_3$ ratios below 100, the $Na^+/TPA^+$ system achieves better crystallization than the $TPA^+$-system, while at ratios above 100 the Na cation is said not to play an important role in crystallization. Increasing the $H_2O/SiO_2$ ratio was found to decrease the crystallization rate. Finally, as the $(TPA)_2O/SiO_2$ and $SiO_2/Al_2O_3$ ratios were increased in a mono cation $TPA^+$ system, larger well defined crystals were observed to form having a barrel shape. Catalyst performance is not reported for any of the synthesized zeolites.

It is appropriate to mention that Nakamoto et al as well as many of the hereinafter discussed articles mention the "alkalinity" of the reaction mixture. The concept of increasing or decreasing alkalinity is to be distinguished from increasing or decreasing pH. When relatively strong bases such as NaOH or TPAOH are present in the reaction mixture, the pH of the same will almost always be 14. Thus, as more base is added while the alkalinity may increase, the pH will remain at 14.

For example, while FIG. 1 of Nakamoto et al illustrates increasing alkalinity, the reaction mixture pH of all of the runs is 14.

A paper by K. Chao, T. Tasi, and M. Chen, entitled "Kenetic Studies on the Formation of Zeolite ZSM-5", Journal of Chem. Soc. Trans. 1, Vol. 77, pp. 547-55 (1981) (hereinafter Chao et al) discloses the effects on nucleation rate and crystal growth, of varying the initial $SiO_2/Al_2O_3$ ratio, alkalinity, and reaction temperature during zeolite synthesis from $Na^+/TPA^+$ aluminosilicate gels. While sulfuric acid is disclosed as one of the reagents used in the experimental section, neither the amount nor the manner in which it is used is reported. The only sodium free gel prepared was also alumina free. In this regard it is noted that an alumina free gel has no cationic sites requiring charge compensation by a metal cation. Chao et al propose that alkalinity of the hydrogel affects the nucleation rate through two mechanisms, namely (1) the dissolution of the gel materials and formation of $Al(OH)n$, and (2) the polymerization of dissolved silicate and aluminate ions to form aluminosilicate or polysilicate ions which can act as a source of nuclei. From the data presented, the authors propose that increasing the alkalinity of the reaction mixture (a) increases dissolution of silicate species of the hydrogel, thereby shortening the induction period (i.e. increasing nucleation rate), but (b) eventually results in restriction of the aforedescribed polymerization thereby lengthening the induction period at very high alkalinity. Chao et al therefore conclude that to achieve the highest nucleation rate an optimum alkalinity can be established where the dissolution and polymerization phenomenon are maximized. On the other hand, alkalinity is said to have almost no effect on the rate of crystal growth. The $SiO_2/Al_2O_3$ ratio is alleged to have a two fold effect on reaction kenetics, namely, (1) except at low alkalinity, the lower the ratio (i.e. more aluminum) the higher the alkalinity needed to attain the aforedescribed optimum alkalinity point (since aluminum consumes $OH^-$ ions forming $Al(OH)n$) and (2) at low levels of alkalinity, the higher the ratio the faster the crystal growth rate. For an aluminum and sodium free system, excess TPAOH was required to achieve the comparable levels of alkalinity to compensate for omission of sodium hydroxide. The sodium/aluminum free system, however yielded only 16% crystallinity (see Table 3). While alkalinity of the reaction system is discussed in great detail, the pH of the reaction mixtures associated with the various alkalinities disclosed is never mentioned. However, it has been determined that the only Na free run disclosed in Chao et al achieves a pH of 14. Furthermore, the catalyst performance of the zeolites prepared by Chao et al was never tested and hence there is no correlation between alkalinity and/or pH on catalyst performance.

In the article, "Growth of Larger Crystals of ZSM-5 in the System 4 $(TPA)_2O$—38 $(NH_4)_2O$—X(Li, Na, K)$_2$O—$Al_2O_3$— 59 $SiO_2$— 750 $H_2O$" by A. Nastro and L. Sand, Zeolites, Vol. 3, pp. 56-62, (1983) (hereinafter Nastro et al), kenetic crystallization data is provided for the growth of ZSM-5 crystals. The authors conclude that the alkali metal free, binary cation system of $TPA^+/NH_4^+$ results in the formation of HZSM-5 after calcination, but the nucleation time, rate of crystallization, and crystal size is much less, relative to those systems which additionally have a small amount of alkali metal present in the initial hydrogel.

The crystallization kenetics of the $NH_4^+/TPA^+$ system were further studied in the paper "Synthesis and Growth of Zeolite $(NH_4, TPA)$-ZSM-5" by N. Ghamami, and L. Sand, Zeolites Vol. 3, pp. 155-62 (April 1983) (hereinafter Ghamami et al). The use of ammonium hydroxide is implemented instead of an alkali metal cation to eliminate the need for an ion-exchange step for subsequent conversion of ZSM-5 catalyst to the hydrogen from (e.g. typically $Na^+$ is exchanged for $NH_4^+$ and the resulting material calcined to evolve $NH_3$, to produce H-ZSM-5, and decompose the organic cation). In a system using precipitated silica powder, 25% TPAOH and initial $SiO_2/Al_2O_3=28$, the reaction does not proceed or proceeds slowly. Increasing the initial $SiO_2/Al_2O_3$ ratio to 59 gives successful crystallization. This ratio is then used to explore the effect of varying the $NH_4^+/NH_4^+ + TPA^+$ ratio on crystallization. As this latter ratio is decreased (i.e. by increasing TPA and reducing $NH_4^+$ correspondingly) the nucleation and crystallization rates are found to increase. A decrease in the $NH_4^+/NH_4^+ + TPA^+$ ratio also corresponds to an increase in alkalinity which accelerates the reactant dissolution processes. Omitting $NH_4^+$ altogether (i.e., using TPAOH alone) results in spherical crystal aggregates while omitting $TPA^+$ (i.e. using $NH_4^{OH}$ alone) results in an amorphous material (Compositions VI and VII respectively). At 180° C. reaction temperature and a $TPA^+/NH_4^+$ ratio of 5/5, increasing the $SiO_2/Al_2O_3$ ratio of the reaction mixture in the regime of 59; 69; 90 and alumina free, increasing the nucleation and crystallization rates. The pH of the reaction mixtures employed in the first part of this paper (i.e. Compositions I to IX) is never reported, although when compositions I to II were tested as described hereinafter in the Examples section, the pH of these mixtures was found to be 14. In the second part of the paper, TPABr is employed as the TPA source, Ludox AS40 (aqueous colloidal silica) as the silca source, and Reheis F-2000 aluminum hydroxide gel powder as the alumina source. The use of an initial $SiO_2/Al_2O_3$ ratio of 59, and TPABr, rather than TPAOH, reduces the alkalinity of the reaction mixture producing an amorphous material at $NH_4OH/TPABr$ ratios of 1.5 to 10 (Composition II). The use of excess $NH_4OH$ (i.e. $NH_4OH/TPABr=15$; Composition XIV) gives a reaction mixture pH of 12–12.5 and produces euhedral crystals after 5 days. When the initial $NH_4OH/TPABr$ ratio is reduced from 15 (in Composition XIV) to 12.5 (Composition XVI) thereby presumably reducing the initial pH to slightly below the 12–12.5 pH value (of Composition XIV), only 50% of the product is crystalline after 5 days.

It is appropriate to mention that the only initial reaction mixture pH reported in Ghamami et al is that of Composition XIV. This pH value is not actively controlled (e.g. with acid), but is merely a result of the conditions established from the initial amounts and identity of ingredients selected. The TPABr salt is essentially neutral in terms of its effect on pH, and when a mixture containing a $TPABr/NH_4OH/H_2O$ mole ratio of 8:120:750 was prepared as described hereinafter, the pH of this mixture was 14. However, when Ludox AS40, which has a pH of 9.2 was added to the $TPABr/NH_4OH/H_2O$ mixture by the inventors herein, as described hereinafter, the pH of the mixture dropped to about 12. Furthermore, Reheis alumina exhibits a pH of 8.6 and its addition to the reaction mixture can further decrease the pH of the same. Consequently, it has been concluded herein that the identity of the source of the alumina and silica in Composition XIV of Ghamami et al is responsible for the inherent initial 12.5 pH of the same. Additionally, it will be observed that Ghamami et al employ extremely small batches of 7ml each. However, when the size of the batch was scaled up for Composition XIV of Ghamami et al, an amorphous material was obtained.

Furthermore, it has been observed by the inventors herein that the final $SiO_2/Al_2O_3$ ratio imparted to the zeolite will typically be lower than initial ratio used in the reaction mixture. Consequently, the initial $SiO_2/Al_2O_3$ ratio of 59 used to prepare Composition XIV of Ghamami et al will likely be reduced in the final zeolite thereby further increasing an already relatively high initial alumina content.

It is further pointed out that in contrast to the expected pH of Composition XVI of Ghamami et al (e.g. about 12) and the associated reduction in crystallinity to 50%, zeolites prepared in accordance with the pH controlled process of the present invention are 100% crystalline.

The article, "Preparation of Zeolite Catalyst for Synthesis of Lower Olefins from Methanol" by E. Kikuchi, R. Hamana, S. Hamanaka and Y. Morita, J. of Japanese Petroleum Institute, Vol. 24, pp. 275–280 (1981) (hereinafter Kikuchi et al) discloses the preparation, and testing for methanol conversion, of ZSM-5 catalysts. Kikuchi et al examine two catalysts designated A and B. Catalyst A is prepared in accordance with the standard Mobil ZSM-5 technique of U.S. Pat. No. 3,702,886, using silica gel, $TPA^+$ and $NaAlO_2$. Catalyst B is prepared using water glass (92.9% $SiO_2$, 9% $Na_2O$), aluminum nitrate and $TPA^+$. However, sufficient $1N HNO_3$ is added to the reaction mixture for Catalyst B to bring the reaction mixture pH to 10–10.5. As the pH is reduced a gellous solution forms and is stirred. Catalyst samples A and B are then tested for methanol conversion with further testing of Catalyst B at varying $SiO_2/Al_2O_3$ ratios. Comparing Catalysts A and B on a morphological basis, Kikuchi et al report that the size of the crystallites of Catalyst B is about 4 times that ot Catalyst A and that the crystallinity of Catalyst B after 1 day of crystallization is about the same as Catalyst A after 6 days. In terms of catalyst performance, Catalyst B is said to show a selectivity to lower olefins about 1.5 times that of Catalyst A at similar conversion levels. Kikuchi et al conclude that the differences in activity may be attributable to a slight difference in pore structure which cannot be identified by XRD, which in turn may enhance the rate of diffusion of the olefin out of the pores. Increasing the $SiO_2/Al_2O_3$ ratio of Catalyst B is the regime of 50; 202; 362; and 602 results in an increase in selectivity to lower olefins, a decrease in the activity of catalyst, and a decrease in the selectivity to aromatic hydrocarbons. Note that Kikuchi et al do not specify whether the $SiO_2/Al_2O_3$ ratios reported are those of the actual zeolite, or the starting ratios employed in the reaction mixture. It is further noted that while Kikuchi et al appear to be the first workers to employ active pH control with an acid, all systems disclosed therein contain conventional amounts of sodium. In addition, the use of water glass (which is highly basic) in accordance with Kikuchi et al results in the formation of a gel. In contrast no significant gel formation is observed in the process of the present invention. It has also been observed that Kikuchi et al fail to report the degree of $Na^+$ exchange, and whether the exchange is conducted before or after calcination.

European Patent Application 93,519 discloses a process for preparing high silica containing zeolites of the ZSM-5 family wherein a buffer is employed to control the pH of the reaction mixture during crystallization between 9.5 and 12. This process is said to be based on the discovery that the final pH of the reaction mixture, will determine the morphology of the resulting crystals. More specifically, a final pH of 10–10.5 is said to produce rod-shaped crystals, a final pH of 12 to 12.5 twinned short prismatic crystals with near spherulitic morphology, and a final pH of 11 to 12, a morphology intermediate between the above noted morphologies. The reaction mixture which is associated with the above morphologies contains water, a source of quaternary ammonium cations, silica, and an alkali metal. An aluminum source is optional. No utility is disclosed for the zeolites prepared in accordance with this process and consequently the activity of such zeolites was never tested for any purpose. The buffers disclosed at Page 3 are conjugate bases, i.e. salts, of a weak acid and a strong base. In contrast, the present invention excludes the presence of alkali metals from the reaction mixture. Furthermore, the activity of the catalysts of the present invention has been found to be dependent on the initial pH of the reaction mixture with buffers being absent when employing a strong acid to control the initial pH.

Moreover, as will be discussed herein, not only does the morphology of the catalysts prepared in the absence of sodium differ from the morphology in the presence of sodium, but the morphology, absent sodium, does not produce the morphological variations, as a function of pH, observed in the above EP application.

U.S. Pat. No. 4,275,047 discloses a process for preparing zeolites such as ZSM-5 wherein the use of alkylammonium ions can be avoided by inclusion in the reaction mixture of a seed zeolite having a specifically defined pore diameter. For unspecified reasons, the reaction mixture is disclosed as preferebly containing one or more anions of strong acids, especially chloride, bromide, iodide or sulphate. Such anions can be introduced as an acid, and/or alkali metal, aluminum, ammonium or onium salts. At Col. 3, Lines 42 et seq, the cryptic comment is made that "if the seed is a member of the ZSM-5 family an appropriate onium compound can be present and thus it is possible to make a product of low alkali content without extensive subsequent ion exchanging and to have additional means of controlling the crystallite size of the product". It is unclear whether the onium compound referred to in the above quote is "present" in the seed, the reaction mixture containing the seed or both, or whether the low "alkali content" referred to is actually intended to refer to alkali metal content or a low concentration of base. In any event, all of the examples contain sodium. Note also that $H_2SO_4$ is employed in Example 5, it is assumed, as a source of sulphate ions.

In the article "Synthesis and Characterization of ZSM-5 Type Zeolites III, A Critical Evaluation of the Role of Alkali and Ammonium Cations" by Z. Gabelica, N. Blum, and E. Derouane, Applied Catalysis, Vol. 5, pp. 227–48 (1983) (hereinafter Gabelica et al), the role of alkali metal and ammonium cations in the nucleation and growth of ZSM-5 zeolites is studied. The authors conclude that the morphology, size, chemical composition and homogeneity of the crystallites depend on competitive interactions between $TPA^+$ or alkali metal cations and aluminosilicate polymeric anions during early stages of nucleation. The crystallization time of a Na free, $TPA^+/NH_4^+$ based system as repeated as 93 days. While both acidic and basic systems are studied, the TPA is added as the bromide salt, and in some instances the pH of the reaction mixture is increased from acidic (e.g. 2–4) to basic (pH 9) by the addition of sodium silicate. One significant observation by Gabelica et al is that the initial $SiO_2/Al_2O_3$ ratio appeared to have little influence on the final zeolite composition, the latter being strongly dependent on the nature of the alkali counterion, which in turn affected the size of the crystallites. For a sodium free $TPA^+/NH_4^+$ based system, the larger the crystallites the higher the Al content. None of the Gabelica et al zeolites are treated for catalyst performance.

From the above discussion it can be seen that ZSM-5 zeolites have been synthesized with organic cations under controlled processing conditions on a sodium free basis, but in the absence of active pH control, although the catalyst performance of such zeolites does not appear to have been tested. On the other hand the use of pH control with an acid has only been applied to sodium-TPA binary cation conventional ZSM-5 systems and the resulting zeolite catalyst exhibits good catalyst performance relative to the absence of pH control.

However, to the best of the inventors' knowledge herein, the combination of the use of an alkali metal free cation reaction system under strict active pH controlled conditions in accordance with the process of the present invention has never been reported, nor has the catalyst performance of zeolites prepared in this manner.

SUMMARY OF THE INVENTION

The present invention is based, inter-alia, on the discovery of the functional relationship between the initial pH of, and the presence or absence of alkali metal cations, such as Na, within, the reaction mixture employed for ZSM-5 type zeolite synthesis, and the ultimate zeolite catalyst performance for olefin synthesis. The control of the reaction mixture pH is an active control requiring the use and presence of an acid. Furthermore, the use of pH control is distinguishable from control of the alkalinity of the reaction mixture in that variations in alkalinity of the reaction mixture do not necessarily result in a variation of the pH of the same. Furthermore, only slight variations of the pH can result in drastic variations in catalyst performance. The natural alkalinity of conventional reaction mixtures can be influenced by the identity and amounts of the silica source, the alumina source, the organic cation source, dilution, and the type of inorganic salts such as $NH_4Br$. Consequently, the natural alkalinity of the reaction mixture will fluctuate uncontrollably in response to changes in one or more such variables.

The amounts and proportions of the components of known sodium free ZSM-5 reaction mixtures are typically not controlled to achieve a particular pH or to impart a particular catalyst performance, but appear to be merely expedients in shortening the duration of zeolite synthesis regardless of the impact on catalyst performance or ultimate initial pH. A short preparation time, however, is not indicative of desirable catalyst performance. Similar considerations apply to the sodium containing reaction mixtures.

A further disadvantage of sodium containing reaction mixtures for low alumina containing zeolites is the difficulty of current sodium exchange techniques to achieve substantially complete exchange on a reproducable basis in batch after batch of catalyst preparation. It is believed that slight variations in the sodium content of final zeolite compositions of low alumina content can significantly affect the acidity of the zeolite needed for olefin synthesis. Consequently, variations in the final sodium content of the zeolite lead to uncontrollable variations in catalyst performance. Thus, by eliminating the presence of cations such as sodium during zeolite synthesis, the problem of sodium exchange variability is eliminated. The presence of sodium during zeolite preparation also significantly affects the crystal morphology of the resulting zeolite even in the presence of active pH control, which in turn can affect ultimate catalyst performance. Such variations in morphology are believed to reflect variations in the way the zeolite components, e.g. Si and Al, are incorporated into the crystal structure. Accordingly, it is an additional advantage of the present invention that a particular zeolite crystal morphology found herein to be associated with excellent catalytic activity in the synthesis of olefins can be consistently reproduced while simultaneously and independently controlling other preparative process variables also found to enhance catalyst performance.

Zeolites prepared by pH control in the absence of sodium perform substantially better than a zeolites prepared under identical conditions of pH control, but in the presence of sodium. Thus, the present invention relies on the combination of two critical variables, namely, active initial pH control and alkali metal, e.g. sodium, exclusion to improve catalyst performance. This technique also permits one to control other synthesis process variables independently of the initial pH of the reaction mixture to maximize catalyst performance.

Accordingly, in one aspect of the present invention there is provided a process for producing a crystalline aluminosilicate zeolite, preferably of the pentasil family, e.g. ZSM-5, which comprises:

(1) admixing to form a reaction mixture substantially free of alkali metal cations:
 (a) at least one tetraalkyl ammonium cation containing compound;
 (b) at least one base in an amount sufficient to impart a pH to the reaction mixture in the initial absence of said acid of (f) of not less than 13 when measured at room temperature;
 (c) at least one silica source;
 (d) at least one alumina source;
 (e) water; and
 (f) at least one acid
in a manner and under conditions sufficient to (i) impart a $SiO_2/Al_2O_3$ mole ratio of from about 70 to about 2000 to the crystalline zeolite; and (ii) adjust, with said acid, the initial pH of the reaction mixture, when measured at room temperature, to be from about 9.0 to about 12.5;

(2) heating the reaction mixture until crystals of said zeolite form; and (3) separating said crystals from the reaction mixture.

In another aspect of the present invention there is provided a process for synthesizing olefins using a zeolite prepared in accordance with the above process and calcined.

TABLE A

Figure 1:
FIGS. 1 to 18 are scanning electron photographs of various zeolites synthesized in accordance with the examples and comparative examples provided hereinafter and summarized at Table 2. The most appropriate details of zeolite synthesis are provided in tabular form on the figures themselves and on Table A below with additional information provided at Table 2.
Figure 2:

| SEM FIG. No. | Power of Magnification | Initial pH of Reaction Mixture | Crystallization Time (Days) | Cation(s) | Ex. or Comp. Ex. No. |
|---|---|---|---|---|---|
| 1 | 2000 | 9.0 | 6 | TPA+ | Ex. 5 |
| 2 | 2000 | 9.5 | " | " | " |
| 3 | 2000 | 10.0 | " | " | Ex. 2 |
| 4 | 2000 | 10.5 | 6(S) | " | Ex. 9, 13 |
| 5A | 2000 | 11.5 | 6 | " | Ex. 1 |
| 5B | 2000 | 11.5 | " | " | Ex. 11, 12 |
| 5C | 2000 | 11.5 | 6(S) | " | Ex. 4, 10 |
| 5D | 2000 | 11.5 | 1 | " | Ex. 6 |
| 5E | 2000 | 11.5 | 3 | " | " |
| 6 | 6000 | 12.0 | 6 | " | Ex. 5 |
| 7 | 2000 | 12.5 | " | " | " |
| 8 | 10,000 | 14.0 | " | " | C. Ex. 1 |
| 9 | 2000 | 10.0 | " | TPA+/NH4+ | Ex. 7 |
| 10A | 2000 | 11.5 | " | " | Ex. 3 |
| 10B | 2000 | 11.5 | 1 | " | Ex. 8 |
| 10C | 2000 | 11.5 | 2 | " | " |
| 10D | 2000 | 11.5 | 3 | " | " |
| 10E | 2000 | 11.5 | 6 | " | Ex. 14 |
| 11 | 2000 | 14.0 | 6 | " | C. Ex. 2 |
| 12 | 2000 | 10.5 | 6 | TPA+/Na+ | C. Ex. 5, C. Ex. 6 |
| 13 | 2000 | 10.5 | 1(S) | " | C. Ex. 3 |
| 14A | 2000 | 11.5 | 6(S) | " | C. Ex. 4, C. Ex. 7 |

TABLE A-continued

| SEM FIG. No. | Power of Magnification | Initial pH of Reaction Mixture | Crystallization Time (Days) | Cation(s) | Ex. or Comp. Ex. No. |
|---|---|---|---|---|---|
| 14B | 10,000 | 11.5 | 6(S) | " | " |
| 15 | 2000 | 12.0 | 6 | TPA Br/NH4+ | C. Ex. 8 |
| 16 | 2000 | 12.0 | 6 | " | C. Ex. 10, Run D |
| 17 | 2000 | 11.5 | 6 | TPA+/NH4+ | Ex. 15 |
| 18 | 2000 | 11.5 | 6 | " | Ex. 16 |

(S) = stirred

DESCRIPTION OF PREFERRED EMBODIMENTS

In accordance with the present invention, nitrogeneous aluminosilicate zeolites, preferably of the ZSM-5 type are produced and then optionally calcined to render them suitable for olefin synthesis.

More specifically, an aluminum source is reacted with a silica source in the presence of a base, preferably a strong base, (a) in the substantial absence of alkali metals, preferably also in the substantial absence of alkaline earth metal cations, (b) in an initial pH adjusted reaction mixture, and (c) in the presence of a tetraalkyl ammonium cation, preferably a tetraalkylammonium hydroxide, containing compound.

The aluminum source must be substantially free of the aforedescribed alkali metal, e.g., sodium, cations and soluble or capable of being solubilized in the reaction mixture under reaction conditions. Thus, the alumina source can be an aluminum salt such as aluminum chloride, sulphate, and/or nitrate, or alumina itself, in a form which is, or can be hydrated such as colloidal alumina, gamma alumina or the alpha or beta aluminum trihydrate as well as mixtures of the above.

The preferred alumina source is aluminum nitrate.

The silica source can be of any type having sufficient chemical reactivity to take part in the zeolite synthesis at an adequate rate and is substantially free of the aforedescribed alkali metal, e.g. sodium, cations. Suitably the silica source is an amorphous silca, such as a colloidal silica e.g., available under the tradename Ludox TM which typically contains 20 to 50% w/w silica in aqueous suspension, fumed silica, precipitated silica, and mixtures of the same. The preferred silica source is colloidal silica.

The tetraalkyl ammonium cation source (TAA+) suitable for use in the present invention is conventional in the synthesis of zeolite type catalysts and each alkyl group thereof contains typically from about $C_1$ to $C_4$ carbons, preferably about $C_1$ to $C_3$ carbons, and most preferably $C_3$ carbons, including tetrapropyl ammonium, and tetraethyl ammonium.

When the TAA+ compound is employed as the hydroxide, the same can constitute the base needed for the reaction mixture. Thus, while the preferred anion of the TAA+ compound is hydroxy, other conventional anions, such as halide, preferably bromide can be employed as the counter ion, provided a sufficient alternative source of hydroxide is employed as described herein. For example, in addition to the tetraalkyl ammonium compound, e.g., hydroxide, the reaction mixture can also contain ammonium hydroxide. The use of ammonium hydroxide base permits a reduction in the amount of the more expensive tetraalkyl ammonium compound, e.g., hydroxide, although the reaction will not proceed as desired in the total absence of the tetraalkyl ammonium compound. Other suitable bases include the alkaline earth metal hydroxides, and methylammonium hydroxide.

The zeolite forming reaction is conducted in accordance with the process of the present invention by heating a suitable aqueous reactant mixture. The initial reaction mixture employed will typically have an initial composition expressed in terms of oxide mole ratios within the following ranges prior to acid addition:

|  | Broad | Preferred | Most Preferred |
|---|---|---|---|
| $(TAA)_2O/SiO_2$ | 0.01 to 5 | 0.05 to 1 | 0.05 to 0.4 |
| $SiO_2/Al_2O_3$ | 80 to 2200 | 110 to 1100 | 220 to 700 |
| $H_2O/SiO_2$ | 10 to 200 | 20 to 140 | 40 to 90 |
| $OH^-/SiO_2$ | 0.02 to 10 | 0.2 to 5 | 0.3 to 3 |
| $(TAA)_2O/(NH_4)_2O$ | 0.01 to $\infty$ | 0.03 to 1000 | 0.05 to 500 |
| $H_2O/OH^-$ | 5 to 500 | 10 to 200 | 20 to 175 | wherein TAA is the sum of the tetraalkyl ammonium cations.

Upon admixing the aforedescribed ingredients typically at room temperature, the reaction mixture will possess an initial pH at room temperature (i.e. between 20° and 25° C.) and prior to adding acid, of typcally not less than about 13, and most preferably about 14. The pH of the reaction mixture is then adjusted by the addition of sufficient organic and/or inorganic acid, preferably inorganic acid, most preferably a strong inorganic acid to a value of typically from about 9.0 to about 12.5, preferably from about 9.5 to about 12 (e.g. 11 to 11.7), and most preferably from about 11.0 to about 11.8 (e.g. 11.3 to 11.7). The term "acid" as used herein in conjunction with pH adjustment is defined to exclude any silica or alumina source with acid properties relative to the base employed.

Furthermore, by strong acid is meant one that reacts completely with the aqueous solvent to give the conjugate acid of the solvent, i.e. $H_3O^+$. A strong base is an ionic hydroxyl compound in the solid state which remains in this form upon solution in water. Preferably, only a strong acids and strong bases are employed and a buffer is not produced in the reaction mixture. Furthermore, the pH of the reaction mixture during crystallization is not controlled.

Suitable inorganic acids include $HNO_3$, $H_2SO_4$, HF, HCl, $HBF_4$, $H_3PO_4$, $H_3BO_3$ and mixtures thereof. Suitable organic acids include acetic acid and propionic acid.

The preferred acids include $HNO_3$ and $HBF_4$. Preferably the acid will decompose during calcination of the zeolite.

Ordinarily, the reaction mixture components are combined by mixing the silica source and the organic base, to form an aqueous solution to which is added the alumina source and the resulting mixture then adjusted for pH.

However, it is also possible, for example, to mix the acid with the alumina source followed by addition of the silica source to give a very low pH of about 1. Base, e.g., TPAOH and/or TPAOH+$NH_4OH$, is then added to achieve the appropriate initial reaction mixture pH and composition as described above.

Passive ajustment of the reaction mixture pH, in the absence of acid, by controlling the amount and identity of alumina or silica reagents, and/or organic base added to the reaction mixture can undesirably produce a wax like gel. Thus, the active use of acid in conjunction with excess base is critical to the present invention although the desired pH can be approached from the low, preferably the high end of the pH scale.

It will be noted, however, that the amount of base to be employed in conjunction with the other reagents to meet the compositional requirements specified hereinabove, and the pH imparted thereby to the reaction mixture in the absence of an acid, will dictate and control the amount of acid employed to achieve the ultimate initial pH, regardless of whether the pH is approached from the high or low end of the pH scale. Consequently, and in view of the above, whether the ultimate initial pH of the reaction mixture is approached from the high or low end of the pH scale, either contingency is considered herein to be an active adjustment of pH with an acid.

Also critical to the present invention is the substantial absence of the aforedescribed cations in the reaction mixture. By substantial absence of a particular cation (e.g. Na) in the initial reaction mixture is meant not greater than 1500, preferably not greater than 800, and most preferably not greater than 200 ppm (e.g. completely free of the cation). Thus, for example, minor contaminant impurities of Na in the reagents used to prepare the initial reaction mixture can be tolerated although this is not preferred. The above maximums of ppm cation content reflect and are based on contaminant amounts of Na found in the form of oxides in commercially available reagents, which form a practical standpoint are difficult to remove. In no event is an alkali metal cation added as an essential ingredient.

After pH adjustment, the reaction mixture may appear cloudy but significant gellation is not observed. The absence of significant gellation permits enhanced aluminum dispersion and consequently, the use of a controlled stirring procedure, hereinafter described, results in a substantial reduction of the crystallite size. It has been found that zeolites of reduced crystallite size prepared by controlled stirring are associated with increased catalyst performance.

The pH adjusted reaction mixture is placed in closed container, such as teflon lined autoclave and heated, typically to a temperature of from about 100 to about 220, preferably from about 120 to about 190, and most preferably from about 140° to about 165° C., until completion of the crystallization, e.g., for a period of typically from about 2.5 to about 10, preferably from about 3 to about 8, and most preferably from about 4 to about 6 days. Generally a minimum of about 3 days, preferably 6 days is needed for complete crystallization. Periods in excess of 6 days are of no apparent advantage.

While crystallization can be conducted at atmospheric, subatmospheric, or superatmospheric pressures in air, it is preferred, to replace the air in the reaction vessel with an inert gas, such as nitrogen under a pressure of from 5 to 100 psi, to avoid possible oxidation of the organic base.

The aforedescribed controlled stirring procedure comprises agitating, e.g., stirring, the reaction mixture during recrystallization for a limited amount of time, and then permitting crystallization for a period of time in excess of the agitation period in the absence of further agitation. Thus, the initial agitation period is conducted for a period of typically from about 1 to about 95, preferably from about 5 to about 30, and most preferably from about 10 to about 18% of the total crystallization time, measured from completion of the pH adjustment. The remainder of the crystallization period is then preferably conducted in the absence of agitation. The period of agitation is typically about 1 day and the static crystallization period is typically about 5 days. The degree of agitation is not critical but should be sufficient to uniformly mix the contents of the reaction mixture (e.g. about 650–1000 rpm). Stirring for the entire crystallization period is also suitable.

The controlled stirring procedure is applicable to either the mono or binary cation system (e.g. TPAOH or TPAOH+NH$_4$OH).

Upon completion of crystallization from the reaction mixture, the product crystals are separated, as by cooling and filtering, and are water washed and dried at a temperature of typically from about 80° to about 120° C.

To be suitable for olefin synthesis, the zeolite obtained will preferably possess a SiO$_2$/Al$_2$O$_4$ mole ratio of at least 70 (e.g. at least 100), typically from about 70 to about 2000, preferably from about 100 to about 1000, and most preferably from about 200 to about 650 (e.g. 200 to 350). As a general rule it has been found that the final SiO$_2$/Al$_2$O$_3$ mole ratio will vary typically from about 10 to about 60% of the initial starting ratio.

The process of the present invention is applicable to the preparation of zeolites which employ a tetraalkylammonium cation and base including ZSM-5 (U.S. Pat. No. 3,702,886); ZSM-11 (U.S. Pat. No. 3,709,979); and ZSM-12 (U.S. Pat. No. 3,832,449); the disclosures of said patents being herein incorporated by reference.

The resulting zeolites are catalytically inactive. Thus, the zeolite is activated for a time effective to remove the organic cations and convert the zeolite to the hydrogen form by calcination at a temperature of typically from about 400 to about 900, preferably from about 450 to about 750, and most preferably from about 500° to about 600° C., preferably in air. Typical calcination times can vary from about 2 to about 15 hours (e.g. 5 to 10 hours).

Ordinarily, when crystallization of the zeolite is conducted in the absence of alkali and alkaline earth metal cations no exchange step is employed. However, if an alkaline earth metal hydroxide is employed as the base, an exchange step is employed to replace the alkaline earth metal cation with a hydrogen cation directly or indirectly with a species of cation which is convertable to the hydrogen cation upon calcination. Such exchange techniques are well known in the art. It is preferred to avoid the use of any exchange step and it is therefore also preferred to avoid the use of an alkaline earth metal hydroxide as the base.

The zeolite catalyst is adaptable to use in the various physical forms in which catalysts are commonly used as particulate material in a contact bed, or a coating material on monolithic structures generally being used in a form to provide high surface area. The catalyst, can if desired, be composited with various catalyst binder or support materials which do not adversely affect the catalyst or the reactions in which the catalyst is to be employed. Representative matrix materials are disclosed in U.S. Pat. No. 4,025,571 at Col. 9, the disclosure of which is herein incorporated by reference.

The reactions conducted in accordance with the use of the zeolites prepared in accordance with the process of the present invention are well known for synthesizing olefins. Such reactions can be broadly characterized by the condensation of certain feed materials to form hydrocarbon mixtures rich in light olefins, e.g., C$_1$ to C$_5$, especially ethylene and propylene. Suitable feeds for this reaction include any monohydric alcohol having from 1 to 4 carbon atoms and/or ethers derived from these alcohols. Thus, methanol, ethanol, n-propanol, isopropanol, n-butanol, sec-butanol and isobutanol may be used either alone or in admixture with one another, or in admixture with ethers derived from such alcohols. Likewise, as noted, ethers such as methylethyl ether and dimethyl ether may be similarly used. Particularly preferred feeds are methanol, dimethyl ether and mixtures thereof.

The alcohols employed in the feed may be manufactured from synthesis gas, i.e., a mixture of CO and H$_2$, from coal, by fermentation, by manufacture from a petroleum fraction in excess supply, or any other suitable means.

More specifically, the process of this invention for using the zeolite herein is preferably conducted such that alcohol and/or ether conversion is carried out in the vapor phase by contact in a reaction zone, such as for example, a fixed bed of catalyst, under effective conversion conditions, said catalyst being characterized as above-defined.

The alcohol and/or ether hydrocarbon conversion process described herein also may be carried out as a batch-type, semi-continuous or continuous operation utilizing a fixed or moving (e.g. fluidized) bed catalyst system. Thus, one embodiment entails use of a catalyst zone wherein the alcohol and/or ether charge is passed concurrently or countercurrently through a moving bed of particle-form catalyst. The latter, after use may be conducted to a regeneration zone wherein coke is burned from the catalyst in an oxygen-containing atmosphere, e.g. air, at an elevated temperature, after which the regenerated catalyst is recycled to the conversion zone for further contact with the alcohol and/or ether feed.

The hydrocarbon feed gas may optionally also contain diluents including any substantially inert substance that is a gas or vapor at reaction temperature. Gaseous nitrogen, carbon dioxide, and carbon monoxide are examples of such materials. Alkanes having up to 3 carbon atoms such as methane, ethane and propane may also be employed as diluents, while C$_4$ and higher carbon number alkanes are undesirable since they are more rapidly converted to coke.

Other hydrocarbon feed additives, which preferably are used in conjunction with an alcohol, e.g. methanol feed, are aromatic hydrocarbon selectivity promoters. Such aromatic promoter compounds include benzene, C$_1$ to C$_5$ (e.g. C$_1$ to C$_2$) alkyl mono or poly substituted benzenes, para-xylene, toluene, and mixtures thereof. The aromatic hydrocarbon promoters are chosen to be of such a size as to be adsorbed into and diffuse within the zeolite pores. While they preferably are reactive towards Bronsted acids they should not irreversibly neutralize the same. The preferred aromatic promoters include benzene, para-xylene and toluene.

The inclusion of the aromatic promoters results in a significant enhancement in olefin selectivity with a moderate drop in conversion of constant reaction conditions relative to the absence of the promoters. It has been found that the inclusion of such aromatic promoters in the feed for use in conjunction with a zeolite prepared as described herein, can slightly diminish catalyst life. However, it has also been found that the inclusion of water (e.g. as steam) in the methanol/aromatic hydrocarbon feed can restore, at least in part, the catalyst life lost as a result of the use of the aromatic promoter, while preserving the selectivity enhancement.

Accordingly, while any amount of aromatic promoter effective to improve the olefin selectivity from methanol may be employed in the hydrocarbon feed, it is contemplated that such effective amount constitute a mole ratio of aromatic to methanol of typically from about 0.2:1 to about .01:1, preferably from about 0.1:1 to about 0.02:1, and most preferably from about 0.07:1 to about 0.04:1.

Likewise, while any amount of water can be employed to improve the catalyst life relative to the absence of said water in the aromatic promoter containing feed, it is contemplated that such effective amount constitute a molar ratio of methanol to water of typically from about 1:0.05 to about 1:0.7, preferably from about 1:0.3 to about 1:0.5, and most preferably from about 1:0.1 to about 1:0.2.

The method of adding the aromatic promoter to the reactor is not critical and will be readily determined by those skilled in the art. Where the aromatic promoter is miscible with a methanol/water feed in the desired proportions it may be simply incorporated into the feed through suitable conventional mixing means before the methanol/water feed is vaporized for introduction into the reactor. Where methanol and water are fed separately to the reactor, the aromatic promoter may also be fed independently or may be mixed first with one of the other feed components, typically methanol, prior to entry into the reactor. An inert carrier gas, typically nitrogen, may also be used to introduce the aromatic promoter.

When dimethyl ether is employed as the reactant in the feed gas either in the presence, and particularly in the absence of methanol, it is preferred to initially include steam in the feed gas. More specifically, the molar ratio of dimethyl ether to steam is typically controlled to be from about 1:5 to about 1:0.2, preferably from about 1:2 to about 1:0.5, and most preferably from about 1:0.7 to about 1:1.2 for a period of typically from about 2 to about 24, preferably from about 4 to about 10, and most preferably from about 5 to about 8 hours, under the hereindescribed reaction conditions. It is most preferred that the catalyst be contacted first with steam alone for a period of typically from about 1 to about 10, and preferably from about 2 to about 5 hours at the hereindescribed reaction temperatures and conditions. It is believed that initial contact of the zeolite with large amounts of DME in the hydrocarbon feed in the absence of water tends to diminish catalyst life by hastened coke deposition. Alternatively, where a mixture of methanol and DME is employed in the reaction feed, it is preferred, in lieu of the initial steam treatment, to optionally initially introduce methanol alone, for the aforedescribed steam conditioning periods, prior to introducing the methanol/DME feed mixture.

When methanol alone is employed as the reactant in the feedstream in the absence of an aromatic promoter, it is preferred to exclude the presence of steam therefrom.

The temperature at which the alcohol and/or ether hydrocarbon conversion process is conducted should be minimized to limit the rate of coke build-up. Accordingly, the temperature of the reaction zone typically will vary from about 250 to about 500, preferably from about 300 to about 450, and most preferably from about 320° to about 360° C.

The feed may be passed over the catalyst at a contact time with the catalyst sufficient to achieve a WHSV of typically from about 2 to about 10, preferably from about 2 to about 7, and most preferably from about 2.5 to about 4 hr$^{-1}$. The reaction pressure typically will be controlled to be about 1 atmosphere. Excessively high pressures alter reaction rates and product selectivity and coking increases significantly.

It can be advantageous to select the combination of temperature, feed rate and pressure conditions such that at least 60 weight percent of the feed reactants are converted to hydrocarbons, and it is particularly preferred to select the combination of conditions so that substantially complete feed conversion is in fact achieved. Furthermore, it is particularly desired to use conditions in the specified ranges that produce conversion to a hydrocarbon mixture comprising a major mole fraction of olefins.

The reaction product effluent from the hydrocarbon conversion process of the present invention contains a hydrocarbon mixture particularly rich in the light olefins, ethylene and propylene, as well as some aromatic hydrocarbons. Generally, a major fraction of the total olefins, calculated on a carbon basis, is ethylene plus propylene. The predominant aromatic hydrocarbons are monocyclic hydrocarbons, notably $C_8$ and $C_9^+$ aromatics. Thus, the predominant hydrocarbons are separated from one another by methods well known in the art.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, conversion, selectivity, and yield are calculated on a % carbon basis as follows:

$$\text{Selectivity (\%)} = \frac{n\,C_n}{\sum_{1 \to i} n\,C_n} \times 100$$

wherein $C_n$ is a hydrocarbon product (excluding dimethyl ether) having in carbon atoms and i is the maximum number of carbon atoms of any compound in the product.

Conversion (%) =

$$\frac{\text{total no. of carbon atoms in product*}}{\text{total no. of carbon atoms in feed}} \times 100$$

*product excludes dimethylether from methanol $$\text{Yield (\%)} = \frac{\text{selectivity} \times \text{conversion}}{100}$$

Catalyst yield is determined by the following equation:

Catalyst yield =

$$\frac{\text{grams of catalyst product}}{\text{sum of weight of all } A_2O_3 + SiO_2 \text{ in initial reaction mixture}} \times 100$$

In the following Examples and Comparative Examples, unless otherwise specified, zeolite synthesis is conducted in a Parr ™ autoclave equipped with a Teflon liner. The liner is cleaned with HF acid prior to each synthesis. Furthermore, prior to sealing the autoclave for each run, the air present therein is purged by flushing with nitrogen and the autoclave then pressurized to 50 to 100 psi with the $N_2$.

Unless otherwise specified, the testing of the zeolites prepared as described hereinafter is conducted in a tube reactor comprising a stainless steel tube having the dimensions: length 36cm, O.D. 1.27cm, and I.D. 1.0cm. The tube is employed n a verticle position. Across the bottom opening thereof is placed a wire mesh screen on top of which is placed glass wool. About 1cc of inert alumina particles ($-30+80$ mesh U.S. sieve series) are placed on top of the glass wool. About 1g of each zeolite tested is then inserted on top of the glass wool and covered with the same, followed by about 1cc of alumina particles, on top of which is placed more glass wool The reactant feed is passed through the top of the reactor and the products collected from the bottom. Reactor effluent samples are analyzed by on line gas chromatography (G.C) at the designated on stream times. Inlet lines to the reactor are placed in a hot box where any liquid feed is vaporized. The reactor is heated in a radiant I.R. furnace and the reaction temperature is determined from thermocouples placed in the upper zone of alumina particles.

Zeolite characterization data obtained for the zeolite samples discussed hereinafter include $SiO_2/Al_2O_3$ mole ratio; % crystallinity obtained through XRD-analysis, acidity equivalents, surface area, average crystal size.

Unless otherwise specified herein, the initial $SiO_2/Al_2O_3$ mole ratio reported at Table 2 is derived from calculations based on the amount of initial materials employed in the synthesis. The final $SiO_2/Al_2O_3$ mole ratio is based on elemental analysis.

The % crystallinity XRD-data was collected on a Phillips ADP-3600 diffractometer using CuK radiation at 45KV, 40MA. Prior to analysis, the samples were placed in a constant humidity atmosphere over a saturated $CaCl_2$ solution. Each sample was scanned in the range $4° < 2° < 100°$. The same treatment was provided for the "standard", and data were collected prior to the other analyses so that direct comparison of intensities could be made.

When the scans were completed, the measured counts for eight peaks in each sample were ratioed to the measured counts for the standard, $(I_{SPL}/I_{STD}) \times 100$. These eight values were subsequently averaged to give the "crystallinity".

Catalyst acidity measurements described herein are determined by measuring the ammonia adsorption of a catalyst sample on a Perkin Elmer TGS-II thermogravimetric analyzer using the following procedure:

1. Tare a clean dry platinum sample pan.
2. Add sample (10-20mg) to the pan and place the pan on the TGS-II balance.
3. Set a flow of 40 ml/min of dry, ultrapure $N_2$ through the top section of the balance and 30 ml/min of the same $N_2$ through the sample chamber.
4. Heat the sample to 500° C. in $N_2$ for 30 minutes to dry it and desorb any materials.
5. Set the furnace temperature to a value of 325° C. at which a measurement is desired.
6. Allow the sample to come to a constant weight in the dry $N_2$ atmosphere and record the weight.
7. Change the gas flowing through the sample chamber to 2% $NH_3$ in $N_2$ with a flow rate of 30 ml/min.
8. Allow the sample to come to a constant weight and record the weight.

9. Wt., % $NH_3$ adsorbed =

$$\frac{\text{wt. in } NH_3 - \text{wt. in } N_2}{\text{wt. in } N_2} \times 100$$

Surface area is determined by the BET method using nitrogen as the adsorbent.

Average crystal size determinations are made from the SEM photographs. More specifically, powder samples were dispersed ultrasonically in a 0.1% ethyl alcohol solution. The prepared samples were then drawn onto cover slips affixed to Al analysis mounts. Gold was next sputtered onto the surfaces to provide conductivity in the SEM. A JSM-U3 scanning electron microscope marketed by JEOL (USA), Inc. of Peabody, Ma was used to produce a magnification series from a representative area of each sample. A 45° tilt angle was imposed during the microscopy phase of study. Each micrograph bears a magnification "micron bar" to enable crystal size determination calculations.

Furthermore, unless otherwise specified flow rates expressed as ml/hr (e.g. of methanol) represent the volume of liquid per hour. Flow rates expressed as ml/min represent the volume of a gas per minute. A 1 gram sample of catalyst is always employed in the reactor unless otherwise specified.

Furthermore unless otherwise specified, a reaction system designated as Na-free is intended to signify the substantial absence of any other alkali metals in the same also. All catalysts employed in the Examples are sodium free. In the Examples and Comparative Examples, when a flow rate is specified for an alcohol containing feed during start-up, the same flow rates are employed for producing product analyzed, unless otherwise specified. All catalyst samples were calcined in accordance with Example 1, Part A, unless otherwise specified. All SEM photographs are of calcined material. Unless otherwise specified, when a start-up procedure employs an alcohol containing feed, the on-stream time is measured starting at initiation of start-up; when start-up employs steam only, the on-stream time is measured starting at completion of start-up.

EXAMPLE 1

This example illustrates a zeolite synthesis with a mono organic cation (TPA+) system on a Na free basis and a pH adjustment to 11.5. Accordingly, 15.21g colloidal silica Ludox AS40 (containing 40% $SiO_2$) were mixed with 45g N-tetrapropyl ammonium hydroxide (25% TPAOH in water). To the first solution was then added a solution of 0.214g $Al(NO_3)_3$ $9H_2O$ dissolved in 5ml $H_2O$. The pH of the mixture was then adjusted with 1N $HNO_3$ from a pH of 14 to a pH of 11.5. The mixture was then placed in a Teflon liner in an autoclave. The autoclave was heated to 150° C. for 6 days in the absence of stirring. The autoclave was then cooled down to room temperature and the solid product was filtered and washed with 800ml distilled water. The product was then dried in the vacuum oven at 120° C. for 16 hours and then calcined at 550° C. with a stream of air flowing at a rate of 20 ml/min for 5 to 10 hours. X-ray analysis showed the material to be highly crystalline. A scanning electron micrograph (SEM) was taken of the calcined material and is presented at FIG. 5A.

The initial reaction mixture composition prior to pH adjustment is summarized in terms of oxide mole ratios at Table 1. Catalyst characterization data are provided at Table 2 Run 1.

Part B

Activation

About 1g of the resulting calcined zeolite having a −30+80 mesh sieve size (U.S. sieve series) was placed in the aforedescribed reactor and subjected to the following activation procedure. A gaseous mixture of nitrogen (20 ml/min) and air (80 ml/min) was passed through the reactor while the temperature thereof was increased automatically by a microprocessor. The temperature profile of the reactor during activation is summarized at Table A below. The temperature profile of Table A is reported in pairs of activation temperatures as a function of time, with the first time period of each pair indicating the transition period during which the reactor temperature is increased from the previously employed reactor temperature to the stated new reactor temperature, and the second time period of each pair indicating the time at which the catalyst is stabilized and maintained at said stated new reaction temperature.

TABLE A

| Reactor Temperature (°C.) | Time (min.) |
| --- | --- |
| 260 | 10 |
| 335 | 10 |
| 335 | 30 |
| 400 | 20 |
| 400 | 30 |
| 450 | 20 |
| 450 | 30 |
| 475 | 10 |
| 475 | 150 |
| 260 | 45 |
| 260 | 60+ |

At the end of the activation procedure, the reactor temperature is stabilized at 260° C. awaiting the introduction of the feed.

Part C

Start-up

Upon completion of the activation procedure, the catalyst was subjected to the following start-up procedure.

A methanol feed flowing at the rate of 3.65 ml/hr was combined with a nitrogen gas diluent flowing at a rate of 20 ml/min, and the resulting mixture passed through the reactor, as the reactor temperature was gradually raised as shown at Table B. The temperature/time profile of Table B shows the period during which the catalyst was stabilized and maintained and the indicated temperature.

TABLE B

| Reactor Temperature (°C.) | Time (hours) |
| --- | --- |
| 260 | 0.5 |
| 300 | 4.5 |
| 320 | 7.0 |

Part D

After start-up, the reactor temperature was increased to 365° C. and maintained thereat for 7 hours, and then lowered to 335° C. and maintained thereat for 39 hours. Product samples were analyzed at the on-stream times shown at Table 2 with zero on-stream time commencing at the beginning of start-up. The results of analysis are shown at Table 2, Runs 1 to 4.

Part E

Upon completion of Part D, the catalyst was regenerated in accordance with the same procedure used for activation in Part B, and then subjected to the same start-up procedure of Part C. Upon completion of start-up the reactor temperature was increased to 335° C. and maintained thereat for about 54 hours at which time the methanol feed was replaced with a 9:1 (V/V) methanol:toluene feed, and this feed passed through the reactor for an additional 31 hours. During the course of this experiment problems developed with the G.C. analyzer and the experiment was terminated. No data is reported herein for this experiment.

Part F

The catalyst was then regenerated as per the activation procedure of Part B, and subjected to the start-up procedure of Part C, with the exception that the methanol flow rate was 3.71 ml/hr.

Part G

Upon completion of the part F start-up, and using the same feed and flow rate, the reactor temperature was increased to 335° C. and maintained thereat for about 51 hours. The reactor temperature was then increased to 360° C. and maintained thereat for about 28 hours. Product samples were removed at the on-stream (beginning at start-up initiation) times shown at Table 2, Runs 5 to 9, analyzed, and the results summarized therein.

EXAMPLE 2

Part A

Figure 3:

This example illustrates the preparation of a mono organic cation (TPA+) at a pH adjustment to 10. Thus, 15.21g colloidal silica Ludox AS40 (composition as described in Example 1) was mixed with 45g N-tetrapropyl ammonium hydroxide (25% TPAOH in $H_2O$). To the first solution was then added a solution of 0.214g $Al(NO_3)_3 \cdot 9H_2O$ dissolved in 5ml $H_2O$. The pH of the reaction was then adjusted with 1N $HNO_3$ from a pH of 14 to a pH of 10. The mixture was then placed in a Teflon liner in an autoclave. The autoclave was heated to 150° C. for 6 days, in the absence of stirring. The autoclave was then cooled down to room temperature and the solid product was filtered and washed with 800ml distilled water. The product was then dried in the vacuum oven at 120° C. for sixteen hours and then calcined for 5 to 10 hours at 550° C. with a stream of air flowing at a rate of about 20 ml/min. X-ray analysis of the calcined material showed that it was highly crystalline. An SEM photograph was also taken and is presented at FIG. 3. Catalyst characterization data are presented at Table 2, Run 10. The initial reaction mixture composition prior to pH adjustment is reported at Table 1.

Part B

The catalyst of Part A was then loaded into the reactor and activated, in accordance with Example 1, Part B, and then subjected to start-up as per Example 1, Part C.

Part C

Upon completion of start-up, the reactor temperature was increased to 335° C. and maintained thereat for 60 hours, and then raised to 360° C. and maintained thereat for 6 hours. However, because the G.C. did not function properly the run was aborted, and the catalyst regenerated in accordance with the activation procedure of Example 1, Part B. No data is reported for this run.

Part D

Upon completion of regeneration, the catalyst was again subjected to start-up as per Example 1, Part C.

Upon completion of start-up, the reactor temperature was raised to 335° C. and maintained thereat for 34 hours. Product was removed at the on-stream times (beginning at start-up initiation) indicated at Table 2, Runs 10 to 12, analyzed and the results summarized therein.

COMPARATIVE EXAMPLE 1

Part A

Figure 8:
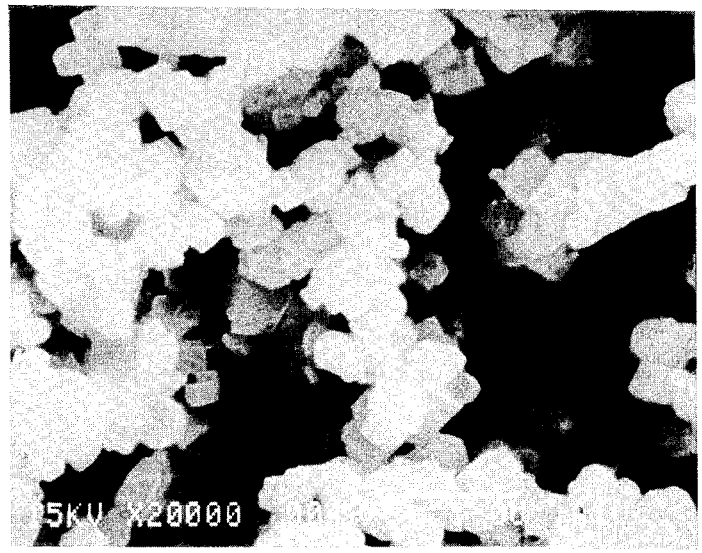

This comparative example illustrates the effect of omitting the pH adjustment in a TPA+ monocation system. Thus, Example 1, Part A was repeated with the exception that no $HNO_3$ was added for pH adjustment. The pH of the reaction mixture was 14. An SEM photograph was taken of the calcined material and is presented at FIG. 8. Catalyst characterization data are also provided at Table 2, Run 13. The initial reaction mixture composition is reported at Table 1.

Part B

The zeolite prepared in accordance with Comparative Example 1, Part A was activated in accordance with Example 1, Part B, and then subjected to the start-up procedure as per Example 1, Part C, with the exception that the following temperature/time profile was employed as summarized at Table C:

TABLE C

| Reactor Temperature (°C.) | Time (hours) |
|---|---|
| 260 | 0.5 |
| 320 | 3.0 |

Part C

Upon completion of start-up, and using a 3.5 ml/hr methanol flow rate, the reactor temperature was raised to 335° C. and maintained thereat for 12 hours. Product samples were removed at the on-stream times (beginning from initiation of start-up) shown at Table 2, Runs 13 and 14, analyzed, and the results summarized therein.

EXAMPLE 3

Part A

This example illustrates the results of employing a binary cation system of TPA+/$NH_4^+$ with pH adjustment to 11.5. Thus, 15.21g colloidal silica (Ludox AS40) was mixed with 9.96g TPAOH (25% solution in $H_2O$), 0.229 mole $NH_4OH$ and 50ml $H_2O$. To this solution was then added 0.214g $Al(NO_3)_3 \cdot 9H_2O$ in 5 ml of $H_2O$. The pH of the resulting reaction mixture was then adjusted with 1N $HNO_3$ from a pH of 14 to a pH of 11.5. The mixture was then placed in a Teflon liner and placed in an autoclave. The autoclave was heated to 150° C. for six days, in the absence of stirring. The autoclave was then cooled down to room temperature and the solid product was filtered and washed with 800ml distilled water. The product was then dried in the vaccuum oven at 120° C. for sixteen hours and then calcined at 550° C. with a stream of air as per Example 1, Part A. Catalyst yield was 95%.

The initial reaction mixture composition prior to pH adjustment is provided at Table 1. Catalyst characterization data is provided at Table 2, Run 15.

Figure 10A:
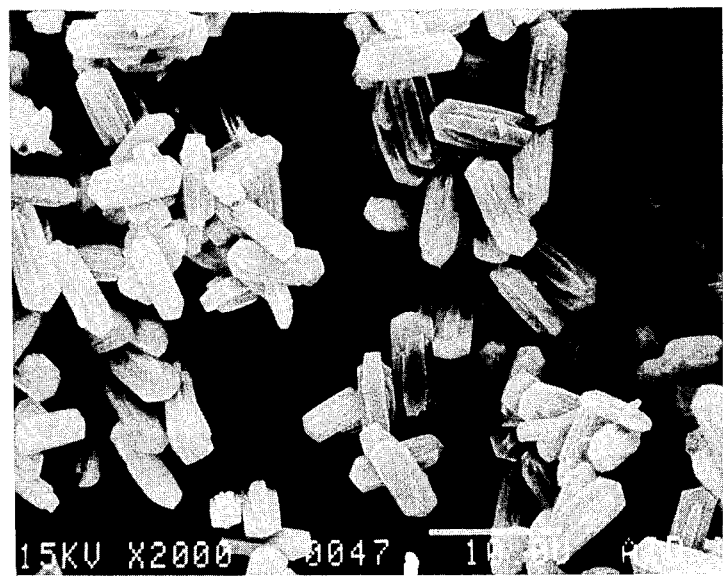

An SEM photograph were taken of the calcined zeolite and is presented at FIG. 10A.

Part B

The catalyst from Example 3, Part A was loaded into the reactor and activated as per Example 1, Part B, and subjected to start-up as per Example 1, Part C, using a methanol flow rate of 3.64 ml/hr. Upon completion of start-up, the reactor temperature was increased to 335° C. and maintained thereat for 35 hours. Product samples were removed at on-stream times (beginning at start-up initiation) as shown at Table 2, Runs 15 and 16, analyzed, and the results summarized therein.

COMPARATIVE EXAMPLE 2

Part A

This Comparative Example illustrates the effect of a TPA+/$NH_4^+$ binary cation system at a pH of 14. Accordingly, 30.42g colloidal silica (Ludox AS40) were mixed with 19.92 TPAOH (25% solution in $H_2O$), 0.229 mole $NH_4OH$ and 50 ml of $H_2O$ to form a first solution. To the first solution was then added a solution of 0.428g $Al(NO_3)_3 \cdot 9H_2O$ in 5 ml $H_2O$. The pH of the reaction mixture was tested and found to be 14. The mixture was then placed in a Teflon liner in an autoclave. The autoclave was heated to 150° C. for six days in the absence of stirring. The autoclave was then cooled down to room temperature and the solid product was filtered and washed with 800 ml distilled water. The product was then dried in the vacuum oven at 120° C. for sixteen hours and then calcined at 550° C. with a stream of air as per Example 1, Part A. Catalyst yield was 90%.

The initial reaction mixture composition prior to pH adjustment was the same as for Example 3. Catalyst characterization data are provided at Table 2, Run 18.

Figure 11:
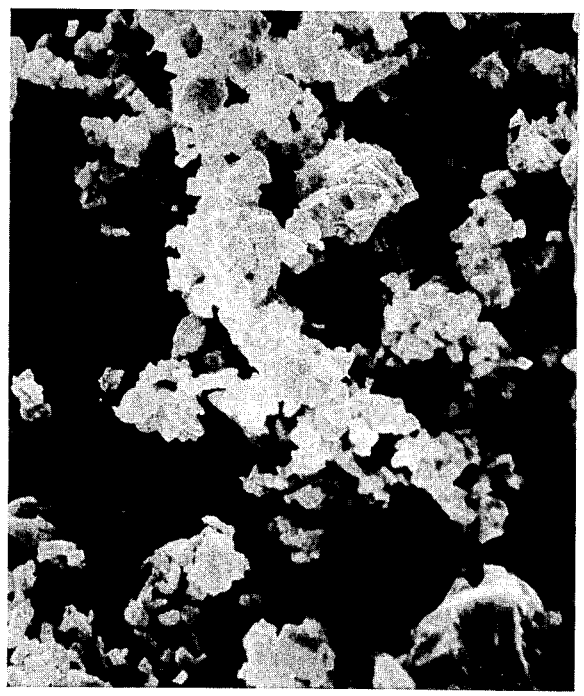

An SEM photograph was taken and is presented at FIG. 11.

Part B

The catalyst from Comparative Example 2 was loaded into the reactor and activated as per Example 1, Part B. The activated catalyst was then subjected to start-up as per Example 1, Part C, using a methanol flow rate of 3.54 ml/hr and a temperature time profile as summarized at Table D.

TABLE D

| Reactor Temperature (°C.) | Time (hour) |
|---|---|
| 260 | 0.5 |
| 300 | 3.0 |
| 320 | 7.0 |

Upon completion of start-up the reactor temperature was raised to 335° C. and maintained thereat for 10 hours. Product samples were removed after the on-stream times (beginning at initiation of start-up) shown at Table 2, Runs 18 and 19, analyzed, and the results summarized therein.

EXAMPLE 4

Part A

This example illustrates the preparation of a zeolite under controlled stirring conditions, a pH of 11.5, and a TPA+ based cation system.

Accordingly, Example 1, Part A was repeated with the exception that the reaction mixture was placed in a Teflon liner in a 300 Ml Fluitron autoclave equipped with a stirrer. The reaction mixture was then stirred at 650 RPM for the first 24 hours of crystallization, and crystallization over the remaining 5 days was conducted in the absence of stirring. All other conditions of the preparation were conducted as per Example 1 including filtration, washing, drying, and calcination. Catalyst characterization data are provided at Table 2, Run 20. An SEM photograph was taken of the catalyst and is presented at FIG. 5C.

Part B

The catalyst from Example 4, Part A was loaded into the reactor, activated, subjected to start-up, and run at 335° C. as per Example 3, Part B. However, because the G.C. analyzer did not function properly, the run was aborted after 28 hours on-stream time.

Part C

After termination of the run of Part B above, the catalyst was regenerated in accordance with the activation procedure of Example 1, Part B, subjected to start-up as per Example 1, Part C, and the temperature then increased to 335° C. and maintained thereat for 39 hours. The temperature was then increased to 360° C. and maintained thereat for 62 hours. Product samples were removed at the on-stream times (beginning upon initiation of start-up) shown at Table 2, Runs 20 to 24, the samples analyzed, and the results summarized therein.

EXAMPLE 5

Part A

This example is intended to illustrate the effect of adjusting the initial pH of the reaction mixture (TPA monocation) to various levels on crystalline morphology, and catalyst performance. Thus, a series of catalyst samples were prepared in accordance with Example 1, Part A, with the only exception that each reaction mixture was adjusted to a different pH with 1N HNO3, namely, the pH was respectively adjusted to 9 (Runs 25–28), 9.5 (Runs 29–34), 12.0 (Run 35), and 12.5 (Runs 36–38). SEM photographs were taken of each sample and are presented at FIGS. 1, 2, 6, and 7. Catalyst characterization data are reported at Table 2, Runs 25, 29, 32, 35 and 36 respectively.

Part B

The catalyst prepared at a pH of 9.0, was loaded into the reactor and activated as per Example 1, Part B, and subjected to start-up as per Example 1, Part C, using a methanol flow rate of 3.54 ml/hr. Upon completion of start-up the reactor temperature was increased to 335° C. and maintained thereat for 29 hours. The temperature was then raised to 360° C. and maintained thereat for 29 hours. Product samples were removed at on-stream times (beginning upon initiation of start-up) as shown at Table 2, Runs 25 to 28, analyzed, and the results summarized therein.

Part C

The testing procedure of Example 5, Part B, was repeated using the catalyst prepared at a pH of 9.5 with the exception that the duration at 335° C. was 30 hours before increasing the temperature to 360° C. for 33 hours. Product samples were removed at on-stream times (beginning at start-up initiation) as shown at Table 2, Runs 29 to 31, analyzed, and the results summarized therein.

Part D

The catalyst employed in Example 5, Part C was regenerated as per Example 1, Part B, using the temperature/time profile shown at Table E.

TABLE E

| Reactor Temp. (°C.) | Time (min.) |
| --- | --- |
| 260 | 30 |
| 335 | 30 |
| 335 | 30 |
| 400 | 30 |
| 400 | 30 |
| 450 | 30 |
| 450 | 30 |
| 475 | 30 |
| 475 | 300 |
| 260 | 45 |
| 260 | 60+ |

The resulting regenerated catalyst was then subjected to start-up as per Example 5, Part B, and thereafter the reactor temperature raised to 335° C. for 30 hours and then to 360° C. for 28.5 hours. Product analysis results at the indicated on-stream times (beginning upon initiation of start-up) are summarized at Table 2, Runs 32 to 34. These results indicate that activity is not completely restored after this regeneration.

Part E

The catalyst prepared at pH 12.0 was not tested.

Part F

The catalyst prepared at pH 12.5 was activated as per the regeneration procedure of Example 5, Part D, subjected to start-up as per Example 1, Part C, using a methanol flow rate of 3.54 ml/hr. The temperature was then increased to 335° C. and maintained thereat for 30 hours and then increased to 360° C. for 45 hours. The run was then terminated due to problems with the methanol delivery pump and a power failure.

Part G

The catalyst from Example 5, Part F, was regenerated as per Example 5, Part D, subjected to start-up as per Example 5, Part B, and the reactor temperature increased to 335° C. and maintained thereat for 27 hours. Product samples were removed at on-stream times (beginning at start-up initiation) shown at Table 2, Runs 36 to 38, analyzed, and the results summarized therein.

EXAMPLE 6

Figure 5A:
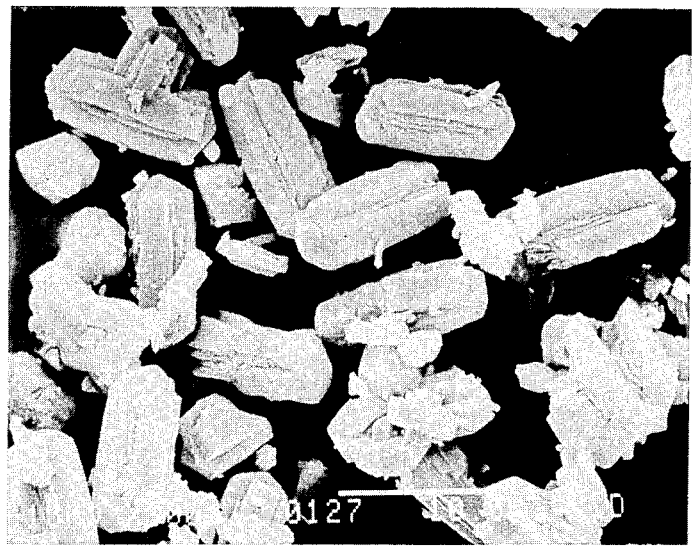

This example is intended to illustrate the effect on crystal morphology and in some instances on catalyst performance, of varying the crystallization time (i.e. time in reactor at crystallization temperature) at an adjusted initial pH of 11.5 with a mono (TPA+) cation based system. Accordingly, Example 1, Part A, was repeated twice with the exception that the crystallization time was shortened to 1 day (Run 39) and then to 3 days (Runs 40-41) for the second preparation. Catalyst characterization data, and test results conducted in accordance with Example 3, Part B are summarized at Table 2, Runs 39 to 41, respectively. SEM photographs were taken of each calcined sample and are presented at FIGS. 5D and 5E.

EXAMPLE 7

Example 3, Part A (TPA+/NH4+) was repeated with the exception that the reaction mixture pH was adjusted to 10.0 instead of 11.5. Catalyst characterization data are summarized at Table 2, Run 42. An SEM photograph was taken of the calcined sample and is provided at FIG. 9.

EXAMPLE 8

This example is intended to illustrate the effect on crystal morphology of variations in crystallization time at an adjusted pH of 11.5 using a binary TPA+/NH4+ cation based system.

Figure 10B:
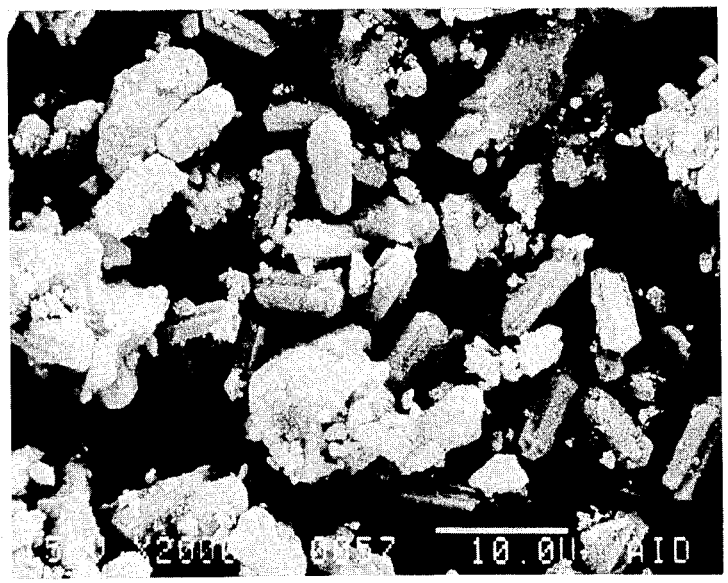
Figure 10C:
Figure 10D:

Accordingly, Example 3, Part A, was repeated three times with the exception that the crystallization time was reduced from 6 days to 1 day (Run 43), 2 days (Run 44), and 3 days (Run 45) respectively. Catalyst characterization data are provided at Table 2. SEM photographs were also taken and are presented at FIGS. 10B, 10C, and 10D, respectively.

EXAMPLE 9

Part A

This example and the following Comparative Example 3 are intended to illustrate the effect on crystal morphology and catalyst performance of the exlusion or inclusion of sodium cations (derived from the use of water glass as per Kikuci et al) in the preparative procedure of a TPA+, 10 to 10.5 pH adjusted, reaction mixture, as per Kikuchi et al. Accordingly, Example 1, Part A, was repeated with the only exception being that the sufficient 1N HNO3 was added to the reaction mixture to reduce the pH thereof from 14 to 10.5, the quantity of all reagents employed were doubled, and the reaction mixture was continuously stirred at 1000 rpm for 6 days. Catalyst characterization data are summarized at Table 2, Run 46. An SEM photograph was taken and is presented at FIG. 4.

Part B

The zeolite prepared in accordance with Example 9, Part A was then loaded into the reactor in accordance with Example 1, Part B, and the subjected to a start-up procedure wherein steam at a temperature of 260° C. was passed over the zeolite for a period of 60 minutes while gradually increasing the temperature thereof to 335° C. After the 60 minute steam start-up treatment the steam was substituted for the methanol (3.5 ml/hr) and N2 (20 ml/min) feed mixture. The catalyst was maintained at 335° C. for 89 hours. The results of product analysis at the indicated on-stream times measured from completion of start-up are summarized at Table 2, Runs 46-57. Catalyst characterization data is also provided at Table 2, Run 46.

COMPARATIVE EXAMPLE 3

Part A

As described above, this comparative example, is intended to illustrate the effect of the presence of sodium in a preparative procedure using pH adjustment to 10-10.5. wherein the sodium is derived from the use of water glass (29% SiO2, 9% Na2O) as the silica source. Where possible, an attempt was made to follow the teachings of Kikuchi et al without defeating the primary purpose of the comparative example. Thus, a 1 day cystallization time with stirring (as per Kikuchi et al) was used. Furthermore, Kikuchi et al are silent regarding the preparation of Catalyst B, as to whether calcination was employed; if it was employed what the conditions of calcination were; as well as the sequence of any calcination in relation to the cation exchange procedure, e.g., cation exchange before or after calcination. Ammonium nitrate was employed for cation exchange rather than HCl as per Kikuchi et al. Since the zeolite is essentially inactive without calcination, it was decided to employ a calcination temperature in accordance with Example 1, i.e. 550° C. Furthermore, calcination was conducted before and after cation exchange.

Accordingly, 52g sodium silicate (DuPont #9), containing 29% SiO2, was mixed with 24.8g n-tetrapropyl ammonium hydroxide (25% TPAOH in water). To this solution was added 34 ml H2O followed by the addition of a solution of 0.448g Al(NO3)3·9H2O dissolved in 8 ml H2O. This mixture was placed in a Teflon liner and the pH was adjusted to 10-10.5 with 1N HNO3. The teflon liner was placed in an autoclave and was charged with 50 psig N2. The autoclave was heated to 150° C. for 1 day with continuous stirring at 1000 rpm.

The autoclave was then cooled down to room temperature and the solid product was filtered and washed with 800 ml distilled water.

The product was then dried in the vacuum oven at 120° C. for 16 hours and then calcined for 5 to 10 hours at 550° C. with a stream of air (20 ml/min). The calcined product was then ion exchanged with 250 ml 1 N NH4NO3. The product was then filtered and washed with water. The ion exchange procedure was repeated 3 times. At the end of ion exchange, the product was filtered, dried in the vacuum oven and calcined as described above.

Zeolite characterization data are provided at Table 2, Run 48. An SEM photograph was taken of the calcined zeolite and is presented at FIG. 13.

Part B

The catalyst from Comparative Example 3 was loaded into the reactor as per Example 1, Part B, and subjected to the start-up procedure as per Example 9, Part B with the exception that the catalyst was stabilized at 335° C. for an additional 60 minutes during the steam treatment.

Part C

Upon completion of start-up, the steam was substituted for a feed containing methanol (3.5 ml/min) and N2 (20 ml/min), which was passed over the catalyst at 335° C. for about 18 hours. Due to problems with the G.C. analyzer, the run was aborted.

Part D

The catalyst from Comparative Example 3, Part C, was regenerated using a gaseous mixture of air (30 ml/min) and N2 (30 ml/min) at 450° C. The regeneration procedure was employed for 18 hours. Upon completion of regeneration, the catalyst was subjected to start-up in steam as per Example 9, Part B. Upon completion of start-up, a methanol/toluene feed (9:1 V/V) was passed over the catalyst at a WHSV of 3.5 hr$^{-1}$ at 335° C. for 70 hours. No data is reported herein for this run.

Part E

The catalyst from Comparative Example 3, Part D, was again regenerated as per Part D, subjected to start-up as per Example 9, Part B, and the catalyst tested using a methanol/N$_2$ feed as per Comparative Example 3, Part C at 335° C. Product samples were removed, at the on-stream times (measured from completion of start-up) shown at Table 2, Runs 48 to 49, analyzed, and the results summarized therein.

EXAMPLE 10

Part A

A portion of the calcined but unused catalyst from Example 4, Part A was employed for this Example. An SEM photograph was taken of the zeolite and presented at FIG. 5C.

Part B

The calcined catalyst from Example 10, Part A was loaded into the reactor as per Example 1, Part B, and subjected to start-up as per Example 9, Part B, in steam. Upon completion of start-up, the steam was substituted for a methanol/benzene (9:1 V/V) feed mixture containing 4 wt.% H$_2$O. This feed mixture, flowing at a WHSV of about 3.7 hr$^{-1}$ was mixed with N$_2$ (20 ml/min) and the resultant mixture passed through the reactor at a temperature of 335° C. for 250 hours. No data is reported herein for this run.

Part C

The catalyst from Example 10, Part B was then regenerated as per Comparative Example 3, Part D, subjected to start-up in steam as per Example 9, Part B, and again contacted with the methanol/benzene/water/N$_2$ feed of Part B above, the methanol/benzene/H$_2$O mixture being introduced at a WHSV of 5.25 hr$^{-1}$. The reaction temperature on-stream time profile (measured from completion of start-up) for this run was as follows:
350° C. / 0 to 15 hours
355° C. / 16 to 87 hours
365° C. / 88 to 96 hours
No data is reported herein for this run.

Part D

The catalyst from Part C, above, was regenerated as per Comparative Example 3, Part D, subjected to start-up as per Example 9, Part B, and Part C of Example 10 repeated using a methanol/benzene/H$_2$O WHSV of 7 hr$^{-1}$ and the following temperature/on-stream time profile:
350° C. / 0 to 20 hours
365° C. / 21 to 48 hours
No data is reported for ths run. The catalyst was regenerated as per Part D of Example 10 and stored for 4 weeks.

Part E

The catalyst from Part D (after storage) was then again regenerated and subjected to start-up as per Example 10, Part D. Upon completion of start-up a feed mixture of phenol/methanol (1:0.34 W/W (WHSV 3.5 hr$^{-1}$) was mixed with N$_2$ (20 ml/min) and the resultant feed passed through the reactor at 335° C. for 20 hours. Problems with the G.C. forced termination of this run.

Part F

The catalyst was regenerated as per Example 10, Part D, with the exception that duration of the regeneration was 65 hours at 450° C. The catalyst was then subjected to start-up as per Example 10, Part D. A methanol/toluene feed (2:1 molar; WHSV 3.5 hr$^{-1}$) was mixed with N$_2$ (20 ml/min) and passed through the reactor at 335° C. for 49 hours. No data is reported herein.

Part G

The catalyst from Part F, was then regenerated as per Example 10, Part D, subjected to start-up and the run of Part F repeated for 24 hours at 335° C. No data is reported herein.

Part H

The catalyst from Part G was then regenerated for 65 hours at 450° C. as per Example 10, Part F, subjected to start-up as per Example 10, Part D, and the run of Part F was repeated for 20 hours using a phenol/methanol (1:4 molar ratio) feed mixture with N$_2$ (20 ml/min). No data is reported herein.

Part I

The catalyst from Part H was then regenerated, subjected to start-up as per Part H, and the run of Part H repeated for 16 hours using a phenol/methanol (1:1 molar) mixture and N$_2$ (20 ml/min). A feed pump malfunction forced the run to be aborted. No data is reported for this run. The catalyst was therefore regenerated as per Example 10, Part D and stored for 4 weeks.

Part J

The catalyst from Part I was taken out of storage, loaded into the reactor as per Example 1, Part B, and subjected to start-up as per Part D of this example. A feed of methanol (WHSV=3.5 hr$^{-1}$) was then mixed with N$_2$ (20 ml/min) and the resultant mixture passed through the reactor at a temperature of 335° C. Product samples were removed at the on-stream times shown at Table (measured upon completion of start-up), runs 50 to 51, analyzed, and the results reported therein.

COMPARATIVE EXAMPLE 4

Part A

This comparative example provides what is believed to be an unobvious modification of the Kikuchi et al TPA$^+$/Na$^+$ preparation of Comparative Example 3, in that the pH of the reaction mixture was reduced to 11.5, rather than 10.5 as in Comparative Example 3. Furthermore, while this comparative example is provided to illustrate the effect of Na at a pH of 11.5 on catalyst performance vis-a-vis the absence of Na as per the present invention, it also represents what is believed to be an embodiment of a separately patentable invention which is the subject of commonly assigned U.S. patent application Ser. No. 685,153, filed on Dec. 21, 1984 (Attorney Docket No. NV-033).

Accordingly, 52g sodium silicate (DuPont #9), containing 29% SiO$_2$, was mixed with 24.8g n-tetrapropyl ammonium hydroxide (25% TPAOH in water). To this solution was added 34ml H$_2$O followed by the addition of a solution of 0.448g Al(NO$_3$)$_3$ 9H$_2$O dissolved in 8ml H$_2$O. This mixture was placed in a Teflon liner and the pH was adjusted to 11.5 with in HNO$_3$. The teflon liner was placed in an autoclave and was charged with 50 psig N$_2$. The autoclave was heated to 150° C. for 6 days with stirring at a rate of 1000 rpm.

The autoclave was then cooled down to room temperature and the solid product was filtered and washed with 800ml distilled water.

The product was then dried in the vacuum oven at 120° C. for 16 hours and then calcined for 5 to 10 hours at 550° C. with a stream of air (20 ml/min). The calcined product was then ion exchanged with 250ml 1 N NH$_4$NO$_3$. The product was then filtered and washed with water. The ion exchange procedure was repeated 3 times. At the end of the exchange, the product was dried in the vacuum oven and calcined as described above. Catalyst characterization data is provided at Table 2, Run 52. SEM photographs were taken and are presented at FIGS. 14A and 14B.

Part B

The catalyst from Part A of this example was loaded into the reactor as per Example 1, Part B, subjected to start-up as per Example 9, Part B, and upon completion of start-up, a methanol (WHSV 3.5 hr$^{-1}$) and N$_2$ (20 ml/min) feed was passed through the reactor at 335° C. for 120 hours. Product samples were removed at the on-stream times (beginning at start-up completion) shown at Table 2, Runs 42 to 56, analyzed, and the results summarized therein.

EXAMPLE 11

Part A

Example 1, Part A was repeated (e.g. pH 11.5, no stirring during 6 day reaction time). Catalyst characterization data is provided at Table 2, Run 57. An SEM photograph was taken and presented at FIG. 5B.

Part B

The calcined zeolite from Part A above, was subjected to steam start-up in accordance with Example 9, Part B. Upon completion of start-up, the catalyst was tested as per Example 12. Upon completion of the runs of Example 12, the catalyst was regenerated as per Comparative Example 3, Part D, subjected to start-up as per Example 9, part B, and then contacted with a methanol (3.5 ml/hr) and N$_2$ (20 ml/min) feed at 335° C. Product samples were removed at the on-stream times (beginning at start-up completion) shown at Table 2, Runs 57 to 60, analyzed, and the results summarized therein.

COMPARATIVE EXAMPLE 5

Part A

Comparative Example 3 (e.g. TPA$^+$/Na$^+$; pH 10.5) was repeated with the exception that one-half quantities of reagent were used and crystallization time was increased from 1 day to 6 days, and no stirring was employed. Catalyst characterization data is provided at Table 2, Run 61. An SEM photograph was taken and is presented at FIG. 12.

Part B

The zeolite prepared in accordance with Comparative Example 5, Part A, was tested in accordance with Example 9, Part B. The total on-stream time was 90 hours measured from completion of start-up. The results are summarized at Table 2, Runs 61 to 64.

EXAMPLE 12

This example is intended to illustrate the effect of including an aromatic promoter in the feed.

Accordingly, the fresh catalyst sample prepared in accordance with Example 11, Part A (pH 11.5) was tested in accordance with Example 9, Part B with the exception that the methanol feed was replaced with a feed containing methanol and toluene (WHSV=3.5$^{hr-1}$) at a volume ratio thereof of 9:1 and N$_2$ (20 ml/min). The results of product testing are summarized at Table 2, Runs 65-67. This catalyst was then regenerated and used for Example 11, Part B, Runs 57 to 60.

COMPARATIVE EXAMPLE 6

This comparative example is intended to provide a basis for comparison with Example 12, using a sodium based preparation representative of Kikuchi et al (pH 10.5) but using a 6 day crystallization time in the absence of stirring.

Accordingly, the sample of catalyst tested in Comparative Example 5 was regenerated, after the 90 hours on-stream time of Comparative Example 5, as per Comparative Example 3, Part B, subjected to start-up as per Example 9, Part D, tested in accordance with Example 12, using the same methanol:toluene (9:1) V/V, N$_2$ feed and flow rates. The results are summarized at Table 2, Runs 68 to 70.

COMPARATIVE EXAMPLE 7

The sample of catalyst prepared and tested in accordance with Comparative Example 4, Parts A & B was regenerated, after 120 hours on-stream time in Comparative Example 4, as per Comparative Example 3, Part D, subjected to start-up as per Example 9, Part B, and tested in accordance with Example 12 using the same methanol:toluene (9:1) feed and flow rates. The results are summarized at Table 2, Runs 71 to 75.

EXAMPLE 13

The catalyst sample prepared and tested in accordance with Example 9, Parts A & B, was regenerated as per Comparative Example 3, Part D, subjected to start-up as per Example 9, Part B, and tested in accordance with Example 12 using the same methanol:toluene (9:1) feed. The results are summarized at Table 2, Runs 76 and 77.

COMPARATIVE EXAMPLE 8

Part A

This comparative example is intended to illustrate the catalyst performance of the zeolite prepared generally in accordance with Composition XIV of Ghamami et al [4(TPA)$_2$O—60(NH$_4$)$_2$O—Al$_2$O$_3$—59SiO$_2$—750H$_2$O] wherein the TPA is derived from TPABr rather than TPAOH, with the exception that the amount of Al$_2$O$_3$ is reduced sufficiently to impart an initial SiO$_2$/Al$_2$O$_3$ mole ratio of about 200 to the zeolite, which is more suitable for olefin synthesis from methanol, the preparation was scaled up to a larger batch size, and the zeolite was calcined as described hereinafter. It is noted that Ghamami et al conduct all their reactions in an autoclave with a 7ml capacity of which only about 75% (5.25 ml) is used. It is concluded therefrom that Ghamami et al do not stir the reaction mixture. It is further noted that Ghamami et al do not calcine the zeolite, but calcination is employed herein.

Accordingly, 30.42g coloidal silica Ludox AS40 (containing 40% $SiO_2$), 24.087g $NH_4OH$ (29% $NH_3$), 7.29g tetrapropylammonium bromide and 10.86g distilled water were mixed together. To this solution was added 0.1980g alumina (Reheis F-2000, containing 52% $Al_2O_3$). The pH of the solution was measured to be 12. The reaction mixture was placed in a Teflon liner in an autoclave. The autoclave was charged with 50 psig $N_2$ and was heated to 150° C. for 6 days in the absence of stirring. The autoclave was then cooled down to room temperature and the solid product was filtered and washed with 800ml distilled water. The product was dried in the vacuum oven at 120° C. for 16 hours and then calcined for 5 to 10 hours at 550° C. with a stream of air. X-ray analysis showed the material to be highly crystalline.

Zeolite characterization data is summarized at Table 2, Run 78. An SEM photograph was taken of the calcined material and is presented at FIG. 15.

Part B

The zeolite prepared in accordance with Comparative Example 8, Part A, above, was loaded into the reactor as per Example 1, Part B, subjected to start-up as per Example 1, Part C using a methanol flow rate of 3.5 ml/hr and the temperature/time profile presented at Table F:

TABLE F

| Reactor Temperature (°C.) | Time (hours) |
| --- | --- |
| 260 | 0.5 |
| 300 | 2.0 |
| 320 | 9.0 |

Part C

Upon completion of start-up, the reactor temperature was increased to 335° C. and maintained thereat for 28 hours and then increased to 360° C. for 9 hours. Product samples were removed at the on-stream times (measured from initiation of start-up) shown at Table 2, Runs 78 to 82, analyzed, and the results summarized therein.

COMPARATIVE EXAMPLE 9

This Comparative Example is intended to illustrate the pH values of certain of the reaction mixtures prepared in accordance with Chao et al subject to the assumptions made herein. Accordingly 3 reaction compositions illustrated at Table 3, p. 554 of Chao et al, were reproduced, namely, Compositions 3 to 5 (numbering in sequence from the first composition of Table 3 in Chao et al). The component mole ratios of these 3 compositions are reproduced hereinbelow at Table G and are designated Runs A to C. The compositions of Chao et al were prepared in accordance with the procedures described therein with the only exceptions being: for composition 3 of Chao et al (Run A herein): the silica source was a silica gel #QUSOG-760 (obtained from Philadelphia Quartz Co); a solution of TPAOH (25% in water) was used, whereas Chao et al prepared his TPAOH (of unknown concentration) from TPABr; and sufficient water was added to the reaction mixture to obtain the reported $H_2O/OH$ ratio; for composition 4 of Chao et al (Run B herein): a silica gel obtained from BDH was used; and sufficient $H_2SO_4$ (concentrated) was added to achieve the reported $OH/SiO_2$ and $Na_2O/SiO_2$ ratios of 0.1 and 0.4 respectively; for composition 5 (Run C herein) the silica source used was a silica gel from BDH.

As may be seem from Run A, the only Na free reaction mixture composition in Chao et al, the pH of this composition was 14. Further, the reaction mixture composition of Run A was also diluted with water to achieve an $H_2O/OH$ ratio of 225 (not shown). The pH value of 14 did not change. When $Al_2(SO_4)_3 \cdot 18H_2O$ was added to the composition of Run A at an $H_2O/OH$ ratio of 225 and a $SiO_2/Al_2O_3$ mole ratio of 140, the pH remained at 14. Finally when the composition of Run A was diluted with sufficient water to produce an $H_2O/OH$ ratio of 450, the pH dropped slightly to 13 and remained very basic.

For Runs B and C, it was determined that at the high $Na_2O/SiO_2$ ratio of 0.4 and low $OH/SiO_2$ ratio of 0.1 reported in Chao et al, it would be necessary to add acid to achieve the reported $OH/SiO_2$ ratio of 0.1. The acid $H_2SO_4$ was mentioned in the experimental part of this paper but the manner of its use was never specified. Accordingly, sufficient $H_2SO_4$ was added to the reaction mixture compositions of Runs B and C, to maintain the appropriate mole ratio balances specified therein based on the assumption that this was only performed in Chao et al, although there is no way to confirm this assumption. When this was done, the pH of the compositions for Runs B and C was 6 and 9 respectively. Note however, that the compositions of Runs B and C both contained high amounts of sodium as did all but the first three Table 3 compositions of Chao et al.

TABLE G

| Run | $SiO_2/Al_2O_3$ | $H_2O/OH$ | $OH/SiO_2$ | $Na_2O/SiO_2$ | $(TPA)_2O/SiO_2$ | pH |
| --- | --- | --- | --- | --- | --- | --- |
| A | Al free | 100 | 0.2 | 0 | 0.1 | 14 |
| B | 140 | 450 | 0.1 | 0.4 | 0 | 6 |
| C | 140 | 450 | 0.1 | 0.4 | 0.04 | 9 |

COMPARATIVE EXAMPLE 10

This Comparative Example is intended to explore various aspects of the compositions prepared in accordance with Ghamami et al.

Part A

Accordingly, using the following reagents:
Silica Source: QUSO G761
Alumina Source: Reheis F-2000
Reaction mixture Compositions I and II of Ghamami et al were prepared in accordance with the same. QUSO G761 was used as a substitute for QUSO F-20 (employed in Chamami et al) since the latter was discontinued by the manufacturer, Philadelphia Quartz Co. The pH of the reaction mixture compositions was tested and found to be 14 in both instances.

Part B

In the second part of Ghamami et al, compositions were employed using different reagents and TPAOH was replaced with TPABr. Accordingly, using the following reagents:
Silica Source: Ludox AS40
Alumina Source: Reheis F-2000
Reaction mixture Compositions XIV, XIX, and XX of Ghamami et al were prepared as described therein with the following exceptions:

For Composition XIV (Run D herein)

This zeolite was prepared in accordance with Comparative Example 8, Part A, herein, with the exception of using 0.6712g Reheis F-2000 (instead 0.1980). After mixing reagents, the pH of the mixture was 12. A precipitate formed at the bottom of the vessel (as aggregates). An SEM photograph was taken of this zeolite and is presented at FIG. 16.

For Composition XIX (Run E herein)

This zeolite was prepared in accordance with Comparative Example 8, Part A, herein, with the exception of not using an alumina and increasing the amount of Ludox AS40 to 46.40g. The pH of the reaction mixture was 12.

For Composition XX (Run F herein)

This zeolite was prepared in accordance with Comparative Example 8, Part A, with the exception of increasing the amount of alumina source to 1.342g (of Reheis F-2000).

The pH of the reaction mixture was 11. The reaction mixture gelled up, such gelation did not occur in composition Nos. XIV and XIX.

The initial pH of each reaction mixture composition tested is summarized at Table H, Runs D to F. In addition, the initial $SiO_2/Al_2O_3$ ratio of Composition XIV was increased to 200 by reducing the amount of alumina source employed and the pH of the solution measured. The results are summarized at Table H, Run G. Note that the catalyst preparative procedure, and catalyst testing results, of the composition of Run G on a scaled up batch size are summarized at Comparative Example 8 and Table 2 herein, Runs 78 to 82.

In Run D (Composition XIV) the mixing of TPABr and $NH_4OH$ produced a solution with a pH of 14. However, upon adding the Ludox AS40, which has a pH of 9.2, the pH was lowered to 12, as reported in Ghamami et al. Thus, the silica source acts as a titrating agent and its quantity can affect pH. Moreover, Run D was also reproduced twice, at the scaled up batch size from Ghamami et al discussed above, and in each instance, the resulting material appeared amorphous, i.e. the crystallinity when tested was found to be less than 10%, the alumina precipitated out of the initial mixture (final $SiO_2/Al_2O_3$ mole ratio was found to be 41). Reducing the alumina content to zero in Run E, did not affect the pH. However, when the alumina content was doubled relative to Run D in Run F, the acidity of the alumina source (which has a pH of 8.6) begins to affect the pH of the reaction mixture and a slightly pH reduction from 12 to 11 was observed. Run F produced a gel in the starting mixture. When the alumina content was reduced to provide an initial $SiO_2/Al_2O_3$ mole ratio of about 200, in Run G, while the product appeared crystalline, a significant amount of alumina precipitated out of solution during the mixing step of the reagents.

From the above results, it can be seen that the natural pH of the reaction mixture of Ghamami et al is a result not only of the relative reagent proportions employed in the reaction mixture, but also of the identity of the reagents employed. Furthermore, since there is no active pH control in Ghamami et al, it is impossible to impart a constant initial pH value to the reaction mixture, as one varies the reagent and ratios thereof.

TABLE H

| Run | Ghamami et al Composition No. | $Al_2O_3$ (moles) | $SiO_2$ (moles) | Initial $SiO_2/Al_2O_3$ | pH | Comments |
|---|---|---|---|---|---|---|
| D | XIV | 1 | 59 | 59 | 12 | Alumina precipitated out in the initial mixture. Crystallinity is less than 10%. (See FIG. 16) |
| E | XIX | 0 | 59 |   | 12 | No alumina was introduced |
| F | XX | 2 | 59 | 28 | 11 | Before alumina addition pH = 12. Reaction mixture turned to a gel. |
| G | N/A | 0.259 | 59 | 200 | 12 | Precipitated formed in the initial mixture, product appears crystalline. (See also C. Ex. 8) |

EXAMPLE 14

Part A

This example is intended to illustrate the effect on crystal morphology and catalyst performance of employing pH adjustment starting at acidic conditions with an acid, and raising the pH with the organic base.

Figure 10E:
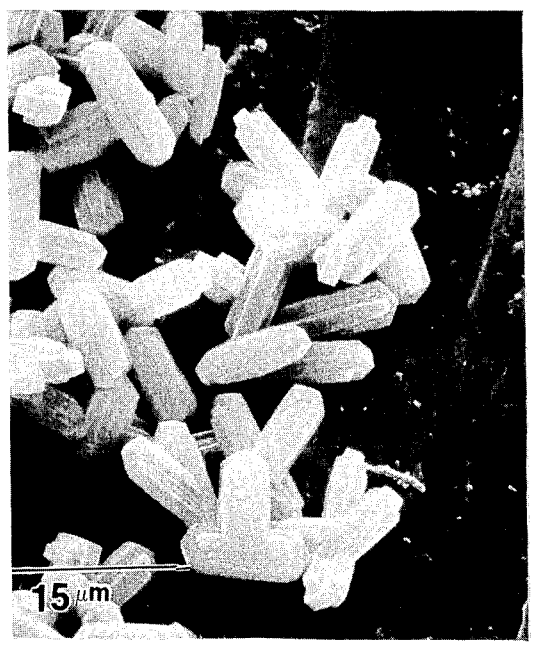

Accordingly, 15.21g coloidal silica Ludox AS40 (containing 40% $SiO_2$), 50ml distilled water, and a solution of 0.214g $Al(NO_3)_3 \cdot 9H_2O$ in 5 ml distilled water were mixed together. To this mixture was then added 12.5ml 1 N $HNO_3$ bringing the pH to about 1. To this mixture was then added a mixture of 9.96g TPAOH (25% solution in $H_2O$) and 13.49g $NH_4OH$. The pH of the reaction mixture was 11.5. The reaction mixture was then placed in an autoclave, heated, recovered and calcined in accordance with the procedure of Example 3. Zeolite characterization data are provided in Table 2, Run 86. An SEM photograph of the zeolite is shown in FIG. 10E.

Part B

The catalyst prepared in accordance with Example 14, was loaded into the reactor as per Example 1, Part B, and subjected to start-up as per Comparative Example 8, Part B. The reactor temperature was then increased to 335° C. and maintained thereat for 28 hours. Product samples were removed at the on-stream times (beginning at start-up initiation) shown at Table 2, Runs 83 to 85, analyzed, and the results summarized therein.

EXAMPLE 15

Part A

This example is intended to illustrate the effect of using $HBF_4$ as the acid for pH adjustment rather than $HNO_3$.

Accordingly Example 3, Part A ($TPA^+/NH_4^+$) was repeated with the exception that $HBF_4$ was employed in place of $HNO_3$ to adjust the initial pH of the reaction mixture to 11.5. The $HBF_4$ acid solution used for pH adjustment was prepared by mixing 10g of 48% $HBF_4$ (remainder water) with 125g deionized water.

Figure 17:
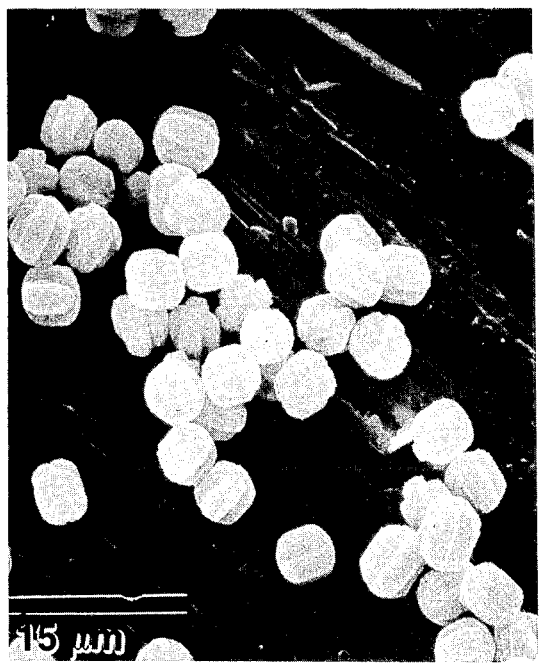

An SEM photograph was taken and presented at FIG. 17. Catalyst characterization data is presented at Run 86.

Part B

The resulting calcined zeolite was loaded into the reactor as per Example 1, Part B, and then activated as per Example 1, Part B with the exception that the reactor was heated to 500° C. for 600 min. in place of heating to 475° C. for 160 min.

Part C

Upon completion of activation the reactor was heated from 260° C. to 300° C. for 2 hours, 320° C. for 9 hours, 335° C. for 27.5 hours and 360° C. for 79 hours using the same feed as employed for activation. Product samples were removed at the on-stream times (measured from the completion of activation) indicated at Table 2, Runs 86 to 89, analyzed, and the results summarized therein.

EXAMPLE 16

Part A

This example is intended to illustrate the effect of employing HF as the acid for pH control.

Accordingly, Example 3, Part A (TPA+/NH$_4$+) was repeated with the exception that HF was employed to adjust the initial pH of the reaction mixture to 11.5, instead of HNO$_3$. The HF solution used to adjust pH was prepared by mixing 4.4g of 48% HF (remainder water) with 125g of deionized water.

Figure 18:
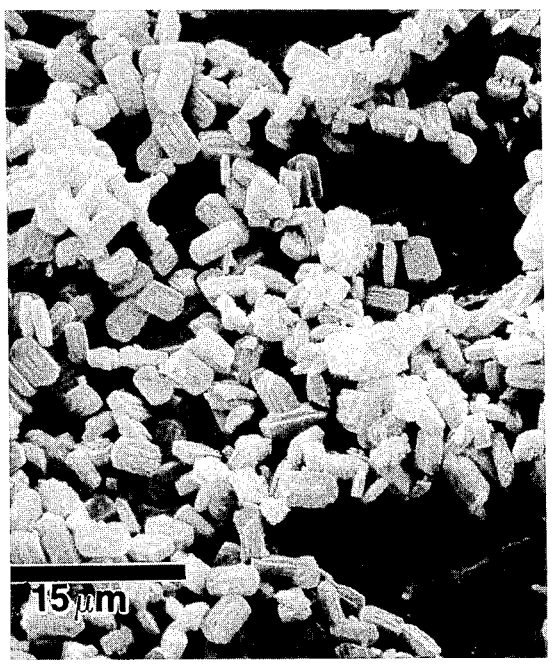

An SEM photograph was taken and the results summarized at FIG. 18. Catalyst characterization data is provided at Run 90.

Part B

The resulting calcined catalyst was loaded into the reactor as per Example 1, Part B, and then activated as per Example 15, Part B.

Part C

Upon completion of activation, the reactor was heated from 260° C. to 300° C. for 2 hours, 320° C. for 9 hours, 335° C. for 27.5 hours, and 360° C. for 37 hours. Product samples were removed from the reactor at the on-stream times indicated (measured from completion of activation) at Table 2, Runs 90 to 93, analyzed, and the results summarized therein.

DISCUSSION OF RESULTS

(A) Catalyst Performance

Referring to Table 2, Runs 1 to 4, it can be seen that starting a reaction temperature of 365° C., results in initially high conversion of 94%. However, as the reaction temperature is decreased to 335° C. conversion drops to about 64% accompanied by an increase in selectivity. In contrast, Runs 5 to 9 indicate that starting at a lower reaction temperature results in a slower decrease in conversion and higher selectivities. For this reason, a reaction temperature of 335° C. is preferred. Referring to Runs 10 to 12, the use of a pH of 10.0 in accordance with the present invention results in a more rapid decrease in conversion relative to a pH of 11.5 (Runs 1 to 9) and lower overall yields. However, when Runs 1 to 12 are compared to Runs 13–14 of Comparative Example 1 (pH 14.0) it can be seen, that the initial conversion at a pH 14.0 is much lower, as are the overall yields relative to use of a pH between 10 and 11.5, and the deactivation of Runs 13–14 occurs much more rapidly to extremely low conversion levels (e.g. 10.7% conversion after only 9 hours on-stream time).

Referring to Runs 15 to 17, it can be seen that a binary cation system of TPA+/NH$_4$+ at a pH of 11.5 results in an even slower deactivation than the corresponding monocation system of TPA only, at the same pH. The binary cation system has the additional advantage in that less TPA+ is required in lieu of the less expensive ammonium cations.

Contrasting Runs 18 and 19 using a TPA+/NH$_4$+ binary cation system at a pH of 14, with Runs 15 to 17, it can be seen that results similar to Runs 13 and 14 (pH 14; TPA+) are obtained, namely, rapid deactivation from an initially very low conversion.

Referring to Runs 20 to 24 of Example 4 and SEM photograph 5C, it can be seen that a 1 day stirring procedure results in a significant decrease in crystallite size which is believed to be associated with the improved performance. For example, after 51 hours on-stream (Run 22) time the conversion is 98.6% in contrast to Run 7 (43 hours on-stream) wherein the conversion has already dropped to 76.2%.

Referring to the runs of Example 5 it can be seen that improved performance in terms of catalyst life and yield is achieved within the pH range of 9 to 12.5 relative to a pH of 14.

Referring to the runs of Example 6, it can be seen that a crystallization time of at least 3 days is preferred to achieve improved catalyst performance.

Comparing the runs of Example 9 TPA; pH=10.5) with those of Comparative Example 3 (TPA+/Na+; pH=10.5) it can be seen that the presence of Na at a pH of 10.5 appears to result in a significant reduction in the catalyst life, e.g. compare 99% conversion after 17 hours (Run 46) without sodium versus 88% conversion after only 7 hours (Run 48) with sodium. However, when the ph of the reaction mixture is increased to 11.5, the presence of sodium at the higher pH unpredictably results in a 7 fold increase catalyst life, but at the expense of a substantial reduction in yield (compare the runs of Example 10 of those of Comparative Example 4). Furthermore, the morphology of the crystals prepared in the presence of sodium is substantially different than that shown for the absence of sodium (compare FIGS. 4 and 13).

Referring to the runs of Example 11 and Comparative Example 5, it can be seen that in the absence of stirring, and at equal crystallization times of 6 days, the modified Kikuchi et al procedure (modified by increasing crystallization time and removing stirring) (TPA+/Na+; pH=10.5) of Comparative Example 5 deactivates much more rapidly than the embodiment (TPA; pH 11.5) of Example 11, and the yield performance of the modified Kikuchi et al procedure also suffers considerably.

Comparing the runs of Example 11 (methanol feed) with those of Example 12 (methanol/toluene feed) (both using TPA+; pH=11.5) it can be seen that at similar on-stream times of 20 hours (Run 60) and 18 hours (Run 67), the introduction of toluene reduces the conversion from 85% to 74% (a proportional decrease of 13%) but results in an increase in selectivity from 42% to 68% (a proportional 61% increase). A similar response to toluene is observed using a TPA+; pH=10.5 catalyst, e.g., compare the runs of Example 9 and Example 13 wherein selectivity at 17 hours on-stream is increased from 27% (Run 46) to 51% (Run 76 at 7 hours on-stream) at the same conversion of 99% by the introduction of toluene.

In contrast, comparing the performance of the catalyst of the runs of Comparative Examples 5 and 6, the modified Kikichi et al catalyst (TPA+/Na+; pH=10.5) is much less responsive to the toluene promoter with respect to both conversion and selectivity, e.g., compare Runs 63 and 70 wherein conversion drops from 61 to 60% and the selectivity increases from 38 to only 40% by introduction of toluene. Note further the overall enhanced yields of the runs of Examples 11 and 12 versus the yields of the runs of Comparative Examples 5 and 6. Similar results are observed vis-a-vis the response to a toluene promoter, by comparison of the runs of Comparative Example 4 versus Comparative Example 7 (TPA+/Na+; pH=11.5). For example, comparing Run 56 with Run 75, it can be seen that the introduction of toluene has substantially no effect on conversion or selectivity at an on-stream time of 111 to 113 hours.

It is concluded that the presence or absence of sodium in conjunction with active pH control not only affects catalyst life and performance, but it also significantly affects the reponsivity of the catalyst to aromatic promoters.

Referring to the runs of Comparative Example 8, the Ghamami et al TPABr/$NH_4^+$, pH=12 (passive control) results in a conversion of 27.2% after only 21 hours on-stream at a yield of 14.2%, an extremely rapid deactivation. In contrasat, the TPA+/$NH_4^+$, pH=11.5 catalyst of the runs of Example 3 exhibits a conversion of 91.6% after 30 hours on-stream and a yield of 33.6%. It is concluded that active control of initial pH with an acid is critical to the process of the present invention and the results obtained thereby. Note further, that the morphology of the catalyst of Ghamami et al (Comparative Example 8) is virtually the same as that of the catalyst of the present invention, while catalyst performance is not. It is therefore also concluded that morphology alone is not indicative of catalyst performance, although differences in morphology can reflect differences in the catalyst preparation procedure.

Referring to the runs of Example 14, it can be seen that approaching the desired pH from the acid side results in similar performance to that obtained when approaching the desired pH from the base side of the reaction mixture, e.g. compare with the results of Example 3.

Referring to the runs of Examples 15 and 16, it is concluded that the use of HF and $HBF_4$ results in an extremely actively catalyst and this activity is maintained for very long periods of time. For example, in Run 89, the conversion is 91.9% afer 113 hours on stream, and in Run 93 it is 100% afer 74.5 hours. Enhanced catalyst life therefore appears to be an additional benefit when employing such acids for pH control.

(B) Catalyst Morphology

Figure 5B:
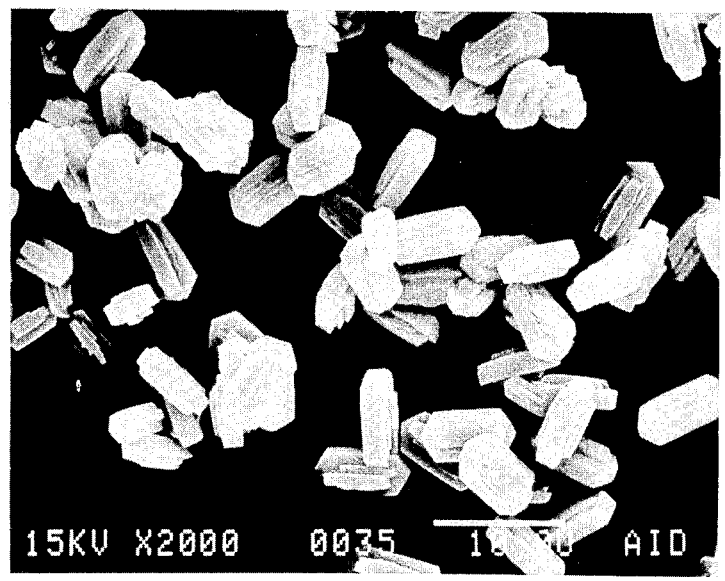

The morphology of the zeolite crystals characteristic of the pH controlled method of the present invention is illustrated most clearly in FIGS. 5B (TPA+; pH 11.5) and 10A (TPA+/$NH_4^+$; pH 11.5).

These zeolites can be described as compound crystals having (i) a primary morphological component characterized as orthorhombic wherein the major exposed and opposed planes possess a hexagonal configuration, and (ii) one or more secondary morphological components characterized as orthorhomic wherein the major exposed and opposed planes possess a retangular configuration; one face of the major exposed plane of the second morphological component being common with, and wholly subsumed within the major exposed plane of the primary morphological component. The preferred zeolite crystals exhibit little or no debris material associated therewith. The length of the hexagonal plane of the crystals generally varies from about 8 to about 15 microns and the width from about 4 to about 8 microns.

Figure 4:

Referring to FIG. 1 (TPA+; pH 9.0) it can be seen that a substantial amount of debris is observed associated with the crystals. The basic morphology however is the same as described above. The amount of debris gradually diminishes as the pH is increased above 9.0; e.g. 9.5 (FIG. 2); 10.0 (FIGS. 3); and is virtually eliminated at a pH of 10.5 (FIG. 4). The amount of debris observed in FIG. 5A is more than has usually been observed at a pH of 11.5. Thus, FIG. 5A is uncharacteristic of the majority of samples observed when prepared at pH of 11.5 vis-a-vis the quantity of debris; FIG. 5B representing the norm for this preparation.

Figure 5C:
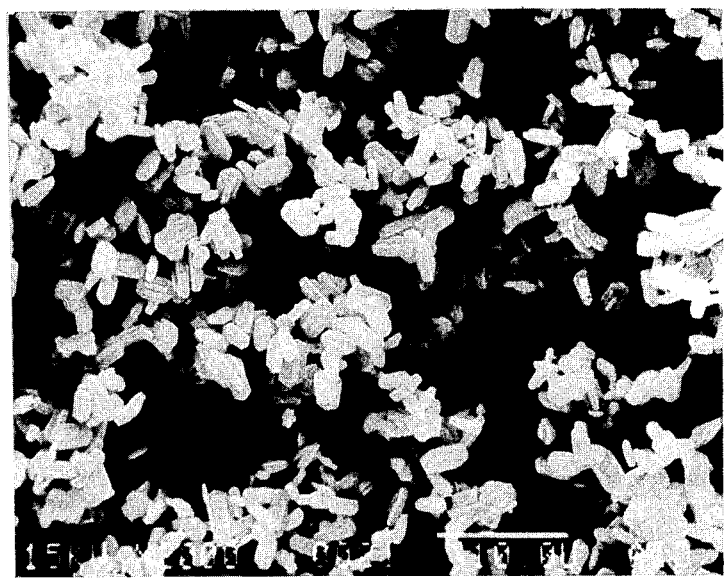

Referring to FIG. 5C it can be seen that stirring of the reaction mixture substantially reduces the size of the crystals to a length of about 2.5 microns and a width of about 1.5 microns. This reduction in size is associated with an improvement in performance. Note, however, that the morphology remains the same.

Figure 5D:
Figure 5E:
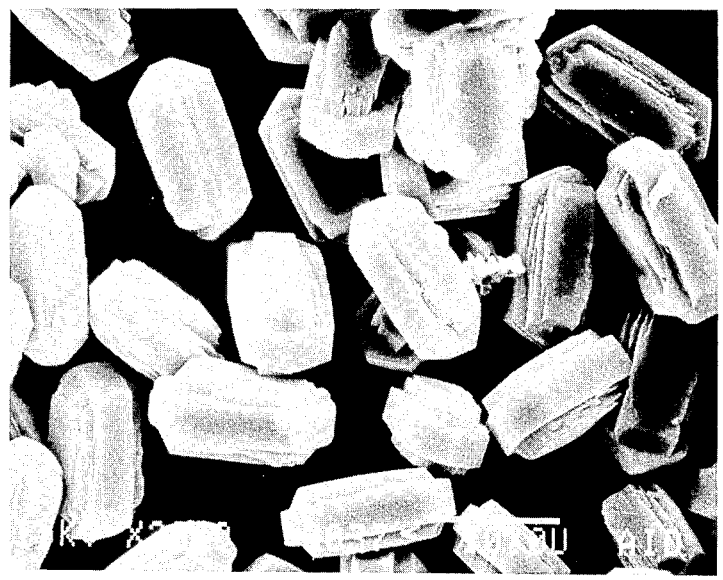
Figure 6:
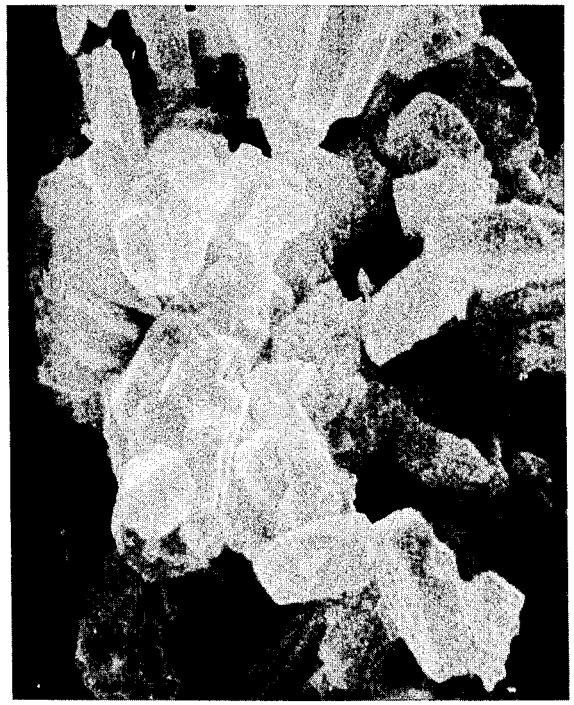

Referring to FIG. 5D it can be seen that incomplete crystallization results after a crystallization time of only 1 day. However, complete crystallization occurs after 3 days (see FIG. 5E).

At a pH of 12.0 (FIG. 6) the gross morphology remains unchanged but the amount of debris is increased relative to a pH of 11.5

Figure 7:
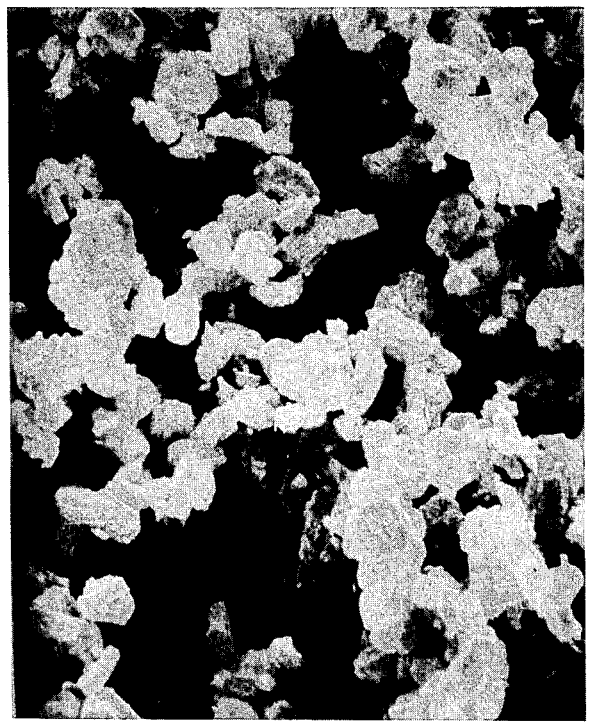

Clumps of crystals having the above described morphology are observed at a pH of 12.5 (FIG. 7).

At a pH of 14 (FIG. 8) the characteristic morphology is absent, with the length and width of the crystals becomming nearly equal. Furthermore, not only do the characteristic second morphological components appear to be absent, but the crystals are highly clumped together in large aggregates. Individual crystals appear hexagonal but with nearly equal dimensions of length, width and thickness. Furthermore, the crystal size is so small that a power of magnification of 10,000X had to be employed to clearly see these crystals.

All of the above discussed figures illustrate the effects of a mono TPA+ cation based preparative procedure in the absence of sodium.

Figure 9:
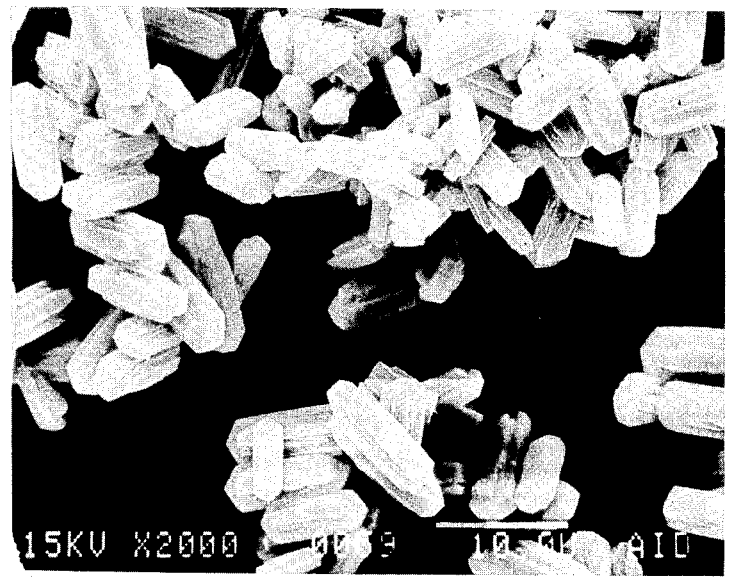

The next series of FIGS. 9 to 11 illustrate the effects of a binary TPA+ /$NH_4^+$ cation based preparative procedure in the absence of sodium. Observations drawn from these figures correspond generally with the observations made from FIGS. 1 to 8. The degree of debris associated with FIG. 10B is non-characteristic at a pH of 11.5; FIG. 10E more closely illustrating the norm. From FIG. 10C it will be observed that nearly complete crystallization has occurred after only 2 days. It is concluded that the inclusion of $NH_4^+$ cations slightly increases the rate of crystallization.

At a pH of 14 (FIG. 11) the crystals again appear to have lost the characteristic morphology. Large aggregates are observed associated with small particles of debris.

Figure 12:
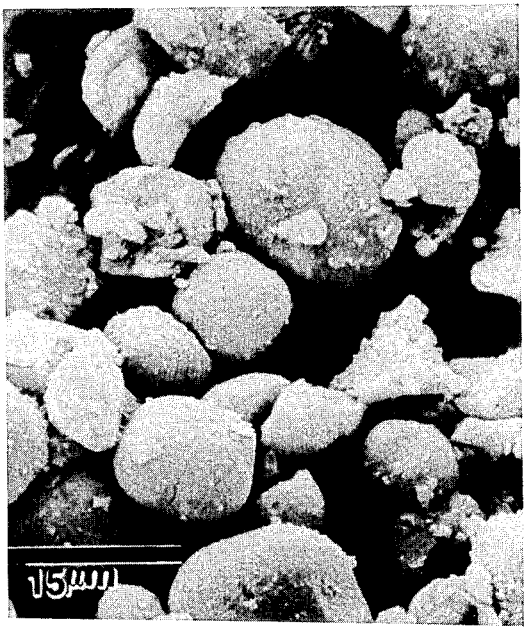
Figure 13:
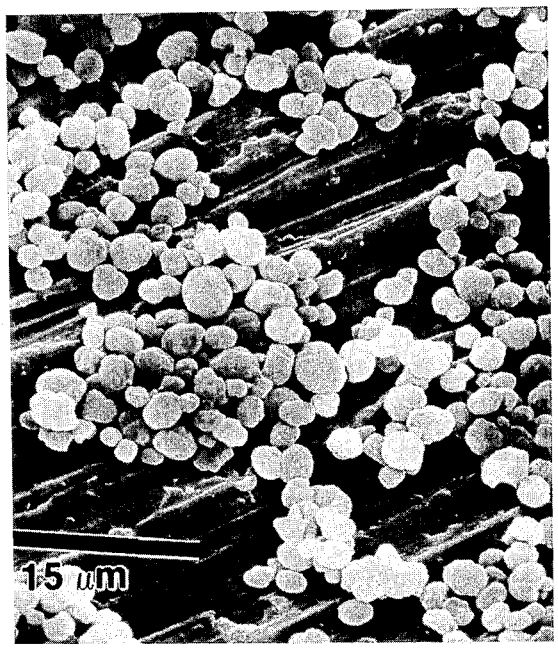
Figure 14A:
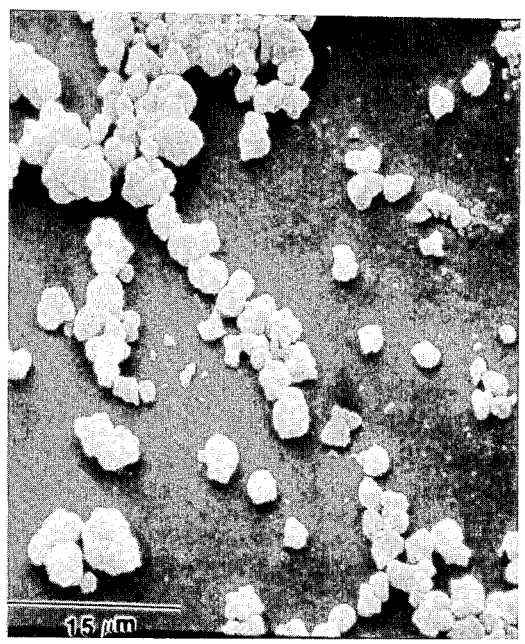
Figure 14B:
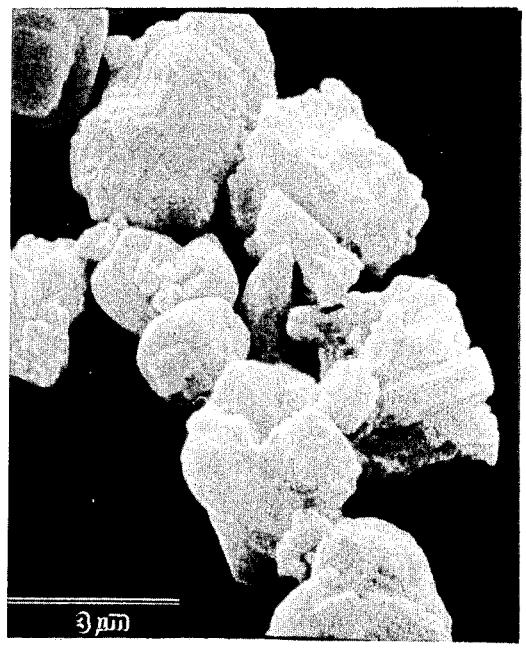

FIGS. 12 to 14 illustrate effects on morphology of including sodium in the preparation. Thus, in the absence of stirring and at a pH of 10.5 (FIG. 12) the crystals appear spherulitic. In the presence of stirring and at the same pH (FIG. 13) the same morphology is observed but the spherulites are much smaller in diameter. Spherulites similarly sized to those of FIG. 13 are observed at a pH of 11.5 (FIG. 14A) in the presence of stirring. However, when the crystals of FIG. 14A are observed under a magnification of 10,000X (FIG. 14B), what initially appeared to be spherulites under 2000X, now appear as crystalline aggregates. Thus, a distinct change in morphology appears to occur in going from a pH of 10.5 to 11.5 in the presence of sodium, namely, a substantial increase in aggregation is observed. This change in morphology is accompanied by significant change in catalyst performance, namely, catalyst life.

Figure 15:

FIG. 15 illustrates a zeolite prepared in accordance with a modification of Ghamami et al (the modification being an increase in the $SiO_2/Al_2O_3$ ratio) using $TPABr/NH_4^+$. While the morphology of these crystals is similar to that of subject invention, catalyst performance is not.

Figure 16:
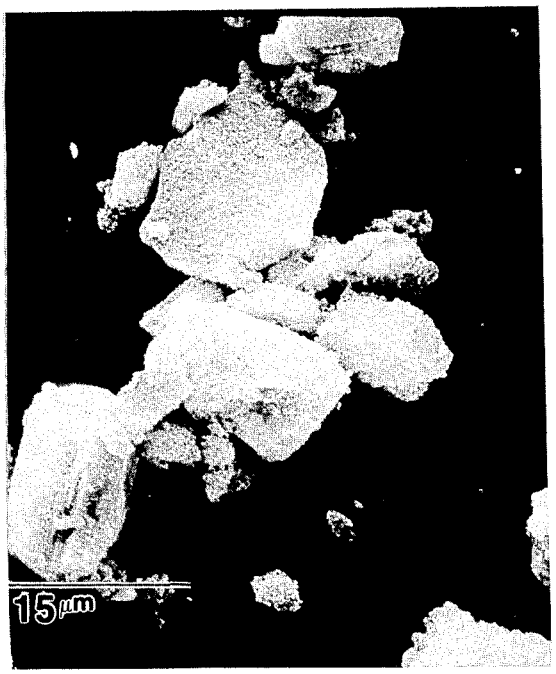

FIG. 16 illustrates an attempted reproduction of Ghamami et al (see Comparative Example 10, Run D). Amorphous particles are primarily produced.

FIGS. 17 and 18 illustrate the effect on morphology of employing $HBF_4$ and HF respectively as the acid for pH adjustment. The use of $HBF_4$ appears to increase the prominence of the second morphological component, while at the same time decreasing the length, and increasing the thickness of the first morphological component relative to its length. The use of HF as the acid does not change the general morphology but does appear to reduce the overall size of the crystals resulting in dimensions similar to but slightly larger than FIG. 5C. The hexagonal edges of the crystals also appear rounded off relative to the angular edges of the samples prepared using nitric acid.

TABLE 1

| Corresponding Ex. or Comp. Ex. No. | $(TPA)_2O/SiO_2$ | $SiO_2/Al_2O_3$ | $H_2O/SiO_2$ | $OH^-/SiO_2$* | $(TPA)_2O/(NH_4)_2O$ | $H_2O/OH^-$** |
|---|---|---|---|---|---|---|
| Ex.1 | 0.274 | 350 | 54 | 0.548 | ∞ | 99 |
| Ex. 2 | 0.274 | 350 | 54 | 0.548 | ∞ | 99 |
| Comp. Ex. 1 | 0.274 | 350 | 27 | 0.548 | ∞ | 49 |
| Ex. 3 | $6.059 \times 10^{-2}$ | 350 | 51 | 2.388 | 0.0534 | 21.6 |

*$OH^-$ derived from bases used and before adding acid
**$H_2O$ includes water from acid addition

TABLE 2

| | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| | CORRES- | | | CATALYST PREPARATION | | | | CATALYST CHARACTERIZATION | | | | | CATALYST TESTING CONDITIONS | | | |
| | PONDING | | | INITIAL | CRYSTAL- | | INI- | FINAL | | | | | | | | | |
| | EX. OR | | | REACTION | LIZATION | | TIAL | SiO$_2$/ | XRD | AVG. SEM | ACID- | | REACT- | ON- | | | |
| | COMP. | SEM | CATION | MIXTURE | TIME | TEMP. | REACTION MIXTURE | Al$_2$O$_3$ | CRYSTAL- | CRYSTAL | ITY | SA | OR | STREAM | | C$_2$= + C$_3$= | |
| RUN. | EX. | FIG. | CATION | pH | (DAYS) | (°C.) | SiO$_2$/Al$_2$O$_3$ | MOLE | LINITY | SIZE | EQ. | (m$^2$/g) | TEMP. | TIME | CONV. | SEL. | YIELD |
| NO. | NO. | NO. | SOURCE | | | | MOLE RATIO | RATIO | (%) | (MICRONS) | (mm/g) | | (°C.) | (HRS.) | (%) | (%) | (%) |
| 1 | EX. 1, PT. D | 5A | TPA+ | 11.5 | 6 | 150 | 350 | 317 | 104 | 7-10 | 88 | 341 | 365 | 13.0 | 94.3 | 30.8 | 29.0 |
| 2 | EX. 1, PT. D | 5A | TPA+ | 11.5 | 6 | 150 | 350 | | | | | | 365 | 18.5 | 97.8 | 30.8 | 30.2 |
| 3 | EX. 1, PT. D | 5A | TPA+ | 11.5 | 6 | 150 | 350 | | | | | | 335 | 23.0 | 73.3 | 44.5 | 32.6 |
| 4 | EX. 1, PT. D | 5A | TPA+ | 11.5 | 6 | 150 | 350 | | | | | | 335 | 33.0 | 63.9 | 46.8 | 29.9 |
| 5 | EX. 1, PT. D | 5A | TPA+ | 11.5 | 6 | 150 | 350 | | | | | | 335 | 18.0 | 93.0 | 38.3 | 36.6 |
| 6 | EX. 1, PT. G | 5A | TPA+ | 11.5 | 6 | 150 | 350 | | | | | | 335 | 37.0 | 80.1 | 46.6 | 37.4 |
| 7 | EX. 1, PT. G | 5A | TPA+ | 11.5 | 6 | 150 | 350 | | | | | | 335 | 43.0 | 76.2 | 46.5 | 34.7 |
| 8 | EX. 1, PT. G | 5A | TPA+ | 11.5 | 6 | 150 | 350 | | | | | | 360 | 68.0 | 93.2 | 39.3 | 36.7 |
| 9 | EX. 1, PT. G | 5A | TPA+ | 11.5 | 6 | 150 | 350 | | | | | | 360 | 80.0 | 76.3 | 47.2 | 36.1 |
| 10 | EX. 2, PT. D | 3 | TPA+ | 10.0 | 6 | 150 | 350 | 389 | 89 | 11-13 | 71 | 306 | 335 | 13.0 | 98.8 | 28.8 | 28.4 |
| 11 | EX. 2, PT. D | 3 | TPA+ | 10.0 | 6 | 150 | 350 | | | | | | 335 | 22.0 | 66.9 | 54.4 | 36.4 |
| 12 | EX. 2, PT. D | 3 | TPA+ | 10.0 | 6 | 150 | 350 | | | | | | 335 | 35.0 | 44.7 | 59.2 | 28.5 |
| 13 | C.EX. 1, PT. B | 8 | TPA+ | 14.0 | 6 | 150 | 350 | 207 | 98 | <1 | 98 | N/A | 335 | 4.0 | 30.4 | 46.4 | 14.1 |
| 14 | C.EX. 1, PT. B | 8 | TPA+ | 14.0 | 6 | 150 | 350 | | | | | | 335 | 9.0 | 10.7 | 44.5 | 4.8 |
| 15 | EX. 3, PT. B | 10A | TPA+/NH$_4$+ | 11.5 | 6 | 150 | 350 | 319 | 89 | 7-8 | 76 | N/A | 320 | 6.0 | 99.8 | 21.0 | 21.0 |
| 16 | EX. 3, PT. B | 10A | TPA+/NH$_4$+ | 11.5 | 6 | 150 | 350 | | | | | | 335 | 18.0 | 99.8 | 24.9 | 24.9 |
| 17 | EX. 3, PT. B | 10A | TPA+/NH$_4$+ | 11.5 | 6 | 150 | 350 | | | | | | 335 | 30.0 | 91.6 | 36.8 | 33.6 |
| 18 | C.EX. 2, PT. B | 11 | TPA+/NH$_4$+ | 14.0 | 6 | 150 | 350 | N/A | N/A | N/A | 29 | N/A | 320 | 4.0 | 21.3 | 47.2 | 10.1 |
| 19 | C.EX. 2, PT. B | 11 | TPA+/NH$_4$+ | 14.0 | 6 | 150 | 350 | | | | | | 335 | 13.0 | 14.4 | 60.7 | 8.8 |
| 20 | EX. 4, PT. C | 5C | TPA+ | 11.5 | 6(S) | 150 | 350 | 296 | 101 | 2.5-3.0 | 53 | | 320 | 7.0 | 99.4 | 17.4 | 17.3 |
| 21 | EX. 4, PT. D | 5C | TPA+ | 11.5 | 6(S) | 150 | 350 | | | | | | 335 | 15.0 | 99.7 | 23.0 | 23.0 |

TABLE 2-continued

| | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| | CORRE-SPONDING | | | CATALYST PREPARATION | | | | | CATALYST CHARACTERIZATION | | | | CATALYST TESTING CONDITIONS | | | | |
| | | | | INITIAL REACTION MIXTURE pH | CRYSTAL-LIZATION | | INITIAL REACTION MIXTURE $SiO_2/Al_2O_3$ MOLE RATIO | FINAL $SiO_2/Al_2O_3$ MOLE RATIO | XRD CRYSTAL-LINITY (%) | AVG. SEM CRYSTAL SIZE (MICRONS) | ACID-ITY EQ. (mm/g) | SA ($m^2/g$) | REACT-OR TEMP. (°C.) | ON-STREAM TIME (HRS.) | | | $C_2^= + C_3^=$ |
| RUN. NO. | EX. OR COMP. EX. NO. | SEM FIG. NO. | CATION SOURCE | | TIME (DAYS) | TEMP. (°C.) | | | | | | | | | CONV. (%) | SEL. (%) | YIELD (%) |
| 22 | PT. C EX. 4, PT. C | 5C | TPA+ | 11.5 | 6(S) | 150 | 350 | | | | | | 335 | 51.0 | 98.6 | 23.1 | 22.8 |
| 23 | EX. 4, PT. C | 5C | TPA+ | 11.5 | 6(S) | 150 | 350 | | | | | | 360 | 59.0 | 99.8 | 17.4 | 17.4 |
| 24 | EX. 4, PT. C | 5C | TPA+ | 11.5 | 6(S) | 150 | 350 | | | | | | 360 | 107 | 81.9 | 34.9 | 31.9 |
| 25 | EX. 5, PT. B | 1 | TPA+ | 9.0 | 6 | 150 | 350 | N/A | 70 | 6-10 | 77 | 267 | 335 | 13.0 | 99.7 | 21.5 | 21.4 |
| 26 | EX. 5, PT. B | 1 | TPA+ | 9.0 | 6 | 150 | 350 | | | | | | 335 | 28.0 | 82.3 | 44.5 | 36.6 |
| 27 | EX. 5, PT. B | 1 | TPA+ | 9.0 | 6 | 150 | 350 | | | | | | 335 | 35.5 | 66.8 | 49.8 | 33.3 |
| 28 | EX. 5, PT. B | 1 | TPA+ | 9.0 | 6 | 150 | 350 | | | | | | 360 | 57.0 | 75.0 | 42.6 | 31.9 |
| 29 | EX. 5, PT. C | 2 | TPA+ | 9.5 | 6 | 150 | 350 | N/A | 92 | 9-10 | 71 | 319 | 335 | 14.5 | 97.0 | 31.5 | 30.5 |
| 30 | EX. 5, PT. C | 2 | TPA+ | 9.5 | 6 | 150 | 350 | | | | | | 335 | 35.5 | 87.4 | 39.8 | 34.8 |
| 31 | EX. 5, PT. C | 2 | TPA+ | 9.5 | 6 | 150 | 350 | | | | | | 360 | 58.5 | 87.7 | 39.7 | 34.8 |
| 32 | EX. 5, PT. C | 2 | TPA+ | 9.5 | 6 | 150 | 350 | | | | | | 335 | 13.0 | 99.7 | 21.5 | 21.4 |
| 33 | EX. 5, PT. D | 2 | TPA+ | 9.5 | 6 | 150 | 350 | | | | | | 335 | 36.0 | 66.8 | 49.8 | 33.3 |
| 34 | EX. 5, PT. D | 2 | TPA+ | 9.5 | 6 | 150 | 350 | | | | | | 360 | 57.0 | 75.0 | 42.6 | 31.9 |
| 35 | EX. 5, PT. D | 6 | TPA+ | 12.0 | 6 | 150 | 350 | N/A | 98 | 4-6 | N/A | 347 | N/A | N/A | N/A | N/A | N/A |
| 36 | EX. 5, PT. E | 7 | TPA+ | 12.5 | 6 | 150 | 350 | N/A | 93 | 3-6 | 59 | 317 | 335 | 15.0 | 99.6 | 22.2 | 22.1 |
| 37 | EX. 5, PT. G | 7 | TPA+ | 12.5 | 6 | 150 | 350 | | | | | | 335 | 23.0 | 89.7 | 42.0 | 37.7 |
| 38 | EX. 5, PT. G | 7 | TPA+ | 12.5 | 6 | 150 | 350 | | | | | | 335 | 35.0 | 48.4 | 52.7 | 25.5 |
| 39 | EX. 6 | 5D | TPA+ | 11.5 | 1 | 150 | 350 | 313 | 64 | 8-9 | 35 | N/A | 335 | 14.0 | 16.7 | 59.1 | 9.9 |
| 40 | EX. 6 | 5E | TPA+ | 11.5 | 3 | 150 | 350 | 320 | 98 | 12-14 | 77 | N/A | 335 | 16.0 | 99.4 | 22.9 | 22.8 |
| 41 | EX. 6 | 5E | TPA+ | 11.5 | 3 | 150 | 350 | 320 | 83 | 6-12 | N/A | N/A | 335 | 27.5 | 83.9 | 44.0 | 36.9 |
| 42 | EX. 7 | 9 | TPA+/NH4+ | 10.0 | 6 | 150 | 350 | 308 | 41 | 5-8 | 59 | N/A | N/A | N/A | N/A | N/A | N/A |
| 43 | EX. 8 | 10B | TPA+/ | 10.0 | 1 | 150 | 350 | | | | | | | | | | |

TABLE 2-continued

| | | | | CATALYST PREPARATION | | | | | CATALYST CHARACTERIZATION | | | | | CATALYST TESTING CONDITIONS | | | | |
|---|---|---|---|---|---|---|---|---|---|---|---|---|---|---|---|---|---|---|
| | | | | INITIAL REACTION MIXTURE pH | CRYSTAL-LIZATION | | INITIAL REACTION MIX-TURE SiO$_2$/Al$_2$O$_3$ MOLE RATIO | FINAL SiO$_2$/Al$_2$O$_3$ MOLE RATIO | XRD CRYSTAL-LINITY (%) | AVG. SEM CRYSTAL SIZE (MICRONS) | ACID-ITY EQ. (mm/g) | SA (m$^2$/g) | REACT-OR TEMP. (°C.) | ON-STREAM TIME (HRS.) | | | C$_2$= + C$_3$= | |
| RUN. NO. | CORRES-PONDING EX. OR COMP. EX. NO. | SEM FIG. NO. | CATION SOURCE | | TIME (DAYS) | TEMP. (°C.) | | | | | | | | | CONV. (%) | SEL. (%) | YIELD (%) |
| 2 | 3 | 4 | 5 | 6 | 7 | 8 | 9 | 10 | 11 | 12 | 13 | 14 | 15 | 16 | 17 | 18 |
| 44 | EX. 8 | 10C | NH$_4$+ | 10.0 | 2 | 150 | 350 | N/A | 89 | 10-15 | N/A | 304 | N/A | N/A | N/A | N/A | N/A |
| 45 | EX. 8 | 10D | TPA+/ NH$_4$+ | 10.0 | 3 | 150 | 350 | N/A | 86 | 11-14 | N/A | 297 | N/A | N/A | N/A | N/A | N/A |
| 46 | EX. 9, PT. B | 4 | TPA+/ NH$_4$+ | 10.5 | 6(S) | 150 | 350 | 370 | N/A | 10-15 | N/A | N/A | 335 | 17.0 | 99.0 | 27.0 | 26.7 |
| 47 | EX. 9, PT. B | 4 | TPA+ | 10.5 | 6(S) | 150 | 350 | 370 | | | | | 335 | 53.0 | 40.0 | 62.0 | 24.8 |
| 48 | C.EX. 3, PT. E | 13 | TPA+/ Na+ | 10.5 | 1(S) | 150 | 400 | 242 | 102 | 2-4 | N/A | 366 | 335 | 7.0 | 88.0 | 25.0 | 22.0 |
| 49 | C.EX. 3, PT. E | 13 | TPA+/ Na+ | 10.5 | 1(S) | 150 | 400 | | | | | | 335 | 22.0 | 58.0 | 48.0 | 27.8 |
| 50 | EX. 10, PT. J | 5C | TPA+ | 11.5 | 6(S) | 150 | 350 | 296 | 101 | 2.5-3.0 | 53 | N/A | 335 | 40.0 | 86.0 | 40.0 | 34.4 |
| 51 | EX. 10, PT. J | 5C | TPA+ | 11.5 | 6(S) | 150 | 350 | | | | | | 335 | 55.0 | 58.0 | 44.0 | 25.5 |
| 52 | C.EX. 4, PT. B | 14A,B | TPA+/ Na+ | 11.5 | 6(S) | 150 | 420 | 302 | N/A | 2-4 | N/A | N/A | 335 | 7.0 | 100.0 | 15.0 | 15.0 |
| 53 | C.EX. 4, PT. B | 14A,B | TPA+/ Na+ | 11.5 | 6(S) | 150 | 400 | | | | | | 335 | 29.0 | 100.0 | 16.0 | 16.0 |
| 54 | C.EX. 4, PT. B | 14A,B | TPA+/ Na+ | 11.5 | 6(S) | 150 | 400 | | | | | | 335 | 92.0 | 100.0 | 19.0 | 19.0 |
| 55 | C.EX. 4, PT. B | 14A,B | TPA+/ Na+ | 11.5 | 6(S) | 150 | 400 | | | | | | 335 | 100.0 | 99.0 | 21.0 | 20.8 |
| 56 | C.EX. 4, PT. B | 14A,B | TPA+/ Na+ | 11.5 | 6(S) | 150 | 400 | | | | | | 335 | 113.0 | 92.0 | 28.0 | 25.8 |
| 57 | EX. 11, Pt. B | 5B | TPA+ | 11.5 | 6 | 150 | 350 | 318 | 114 | 7-8 | 77 | N/A | 335 | 4.0 | 100.0 | 24.0 | 24.0 |
| 58 | EX. 11, PT. B | 5B | TPA+ | 11.5 | 6 | 150 | 350 | | | | | | 335 | 12.0 | 98.0 | 35.0 | 34.3 |
| 59 | EX. 11, PT. B | 5B | TPA+ | 11.5 | 6 | 150 | 350 | | | | | | 335 | 16.0 | 91.0 | 40.0 | 36.4 |
| 60 | EX. 11, PT. B | 5B | TPA+ | 11.5 | 6 | 150 | 350 | | | | | | 335 | 20.0 | 85.0 | 42.0 | 35.7 |
| 61 | C.EX. 5, PT. B | 12 | TPA+/ Na+ | 10.5 | 6 | 150 | 400 | 242 | 97 | 12-16 | N/A | 337 | 335 | 2.0 | 97.0 | 25.0 | 24.2 |
| 62 | C.EX. 5, PT. B | 12 | TPA+/ Na+ | 10.5 | 6 | 150 | 400 | | | | | | 335 | 9.0 | 69.0 | 34.0 | 23.5 |
| 63 | C.EX. 5, PT. B | 12 | TPA+/ Na+ | 10.5 | 6 | 150 | 400 | | | | | | 335 | 11.0 | 61.0 | 38.0 | 23.2 |

TABLE 2-continued

| | | | | CATALYST PREPARATION | | | | | CATALYST CHARACTERIZATION | | | | | CATALYST TESTING CONDITIONS | | | | |
|---|---|---|---|---|---|---|---|---|---|---|---|---|---|---|---|---|---|---|
| | | | | INITIAL REACTION MIXTURE pH | CRYSTALLIZATION | | INITIAL REACTION MIXTURE SiO$_2$/Al$_2$O$_2$ MOLE RATIO | FINAL SiO$_2$/Al$_2$O$_3$ MOLE RATIO | XRD CRYSTALLINITY (%) | AVG. SEM CRYSTAL SIZE (MICRONS) | ACIDITY EQ. (mm/g) | SA (m$^2$/g) | REACTOR TEMP. (°C.) | ON-STREAM TIME (HRS.) | CONV. (%) | SEL. (%) | C$_2^=$ + C$_3^=$ YIELD (%) |
| RUN. NO. | CORRESPONDING EX. OR COMP. EX. NO. | SEM FIG. NO. | CATION SOURCE | | TIME (DAYS) | TEMP. (°C.) | | | | | | | | | | | | |
| 1 | 2 | 3 | 4 | 5 | 6 | 7 | 8 | 9 | 10 | 11 | 12 | 13 | 14 | 15 | 16 | 17 | 18 |
| 64 | C.EX. 5, PT. B | 12 | TPA+/Na+ | 10.5 | 6 | 150 | 400 | | | | | | 335 | 19.0 | 10.0 | 63.0 | 6.3 |
| 65 | EX. 12 (M/T) | 5B | TPA+ | 11.5 | 6 | 150 | 350 | 318 | 114 | 7-8 | 77 | N/A | 335 | 6.0 | 99.0 | 47.0 | 46.5 |
| 66 | EX. 12 (M/T) | 5B | TPA+ | 11.5 | 6 | 150 | 350 | | | | | | 335 | 18.0 | 96.0 | 53.0 | 50.9* |
| 67 | EX. 12 (M/T) | 5B | TPA+ | 11.5 | 6 | 150 | 350 | | | | | | 335 | 18.0 | 74.0 | 68.0 | 50.3 |
| 68 | C.EX. 6 (M/T) | 12 | TPA+/Na+ | 10.5 | 6 | 150 | 400 | 242 | 97 | 12-16 | N/A | 337 | 335 | 2.0 | 91.0 | 31.0 | 28.2 |
| 69 | C.EX. 6 (M/T) | 12 | TPA+/Na+ | 10.5 | 6 | 150 | 400 | | | | | | 335 | 6.0 | 81.0 | 39.0 | 31.6 |
| 70 | C.EX. 6 (M/T) | 12 | TPA+/Na+ | 10.5 | 6 | 150 | 400 | | | | | | 335 | 11.0 | 60.0 | 40.0 | 24.0 |
| 71 | C.EX. 7 (M/T) | 14A,B | TPA+/Na+ | 11.5 | 6(S) | 150 | 400 | 302 | N/A | 2-4 | N/A | N/A | 335 | 20.0 | 100.0 | 28.0 | 28.0 |
| 72 | C.EX. 7 (M/T) | 14A,B | TPA+/Na+ | 11.5 | 6(S) | 150 | 400 | | | | | | 335 | 53.0 | 100.0 | 24.0 | 24.0 |
| 73 | C.EX. 7 (M/T) | 14A,B | TPA+/Na+ | 11.5 | 6(S) | 150 | 400 | | | | | | 335 | 80.0 | 100.0 | 25.0 | 25.0 |
| 74 | C.EX. 7 (M/T) | 14A,B | TPA+/Na+ | 11.5 | 6(S) | 150 | 400 | | | | | | 335 | 109.0 | 100.0 | 27.0 | 27.0 |
| 75 | C.EX. 7 (M/T) | 14A,B | TPA+/Na+ | 10.5 | 6(S) | 150 | 400 | | | | | | 335 | 111.0 | 92.0 | 28.0 | 25.8 |
| 76 | EX. 13 (M/T) | 4 | TPA+ | 11.5 | 6(S) | 150 | 350 | 370 | N/A | 10-15 | N/A | N/A | 335 | 7.0 | 99.0 | 51.0 | 50.5 |
| 77 | EX. 13 (M/T) | 4 | TPA+ | 11.5 | 6(S) | 150 | 350 | | | | | | 335 | 10.0 | 64.0 | 71.0 | 45.4 |
| 78 | C.EX. 8 | 15 | TPA$^{Br}$/NH$_4^+$ | 12.0 | 6 | 150 | 200 | 307 | N/A | 19-21 | N/A | N/A | 320 | 2.0 | 98.8 | 24.9 | 24.6 |
| 79 | C.EX. 8 | 15 | TPA$^{Br}$/NH$_4^+$ | 12.0 | 6 | 150 | 200 | | | | | | 320 | 8.0 | 36.7 | 52.8 | 19.4 |
| 80 | C.EX. 8 | 15 | TPA$^{Br}$/NH$_4^+$ | 12.0 | 6 | 150 | 200 | | | | | | 335 | 14.0 | 83.5 | 52.5 | 34.4 |
| 81 | C.EX. 8 | 15 | TPA$^{Br}$/NH$_4^+$ | 12.0 | 6 | 150 | 200 | | | | | | 335 | 16.0 | 60.8 | 59.5 | 29.6 |
| 82 | C.EX. 8 | 15 | TPA$^{Br}$/NH$_4^+$ | 12.0 | 6 | 150 | 200 | | | | | | 335 | 21.0 | 27.2 | 61.9 | 14.2 |
| 83 | EX. 14 | 10E | TPA+/NH$_4^+$ | 11.5 | 6 | 150 | 350 | 329 | N/A | 9-11 | N/A | N/A | 320 | 6.0 | 95.3 | 27.4 | 26.2 |
| 84 | EX. 14 | 10E | TPA+/NH$_4^+$ | 11.5 | 6 | 150 | 350 | | | | | | 335 | 12.5 | 99.1 | 23.5 | 23.3 |

TABLE 2-continued

| | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| | CORRES- | | | CATALYST PREPARATION | | | INITIAL REAC-TION MIX-TURE | CATALYST CHARACTERIZATION | | | | | CATALYST TESTING CONDITIONS | | | | |
| | | | | | CRYSTAL-LIZATION | | | FINAL | | | | | | | | $C_2^= + C_3^=$ | |
| RUN. NO. | PONDING EX. OR COMP. EX. NO. | SEM FIG. NO. | CATION SOURCE | INITIAL REACTION MIXTURE pH | TIME (DAYS) | TEMP. (°C.) | $SiO_2/Al_2O_3$ MOLE RATIO | $SiO_2/Al_2O_3$ MOLE RATIO | XRD CRYSTAL-LINITY (%) | AVG. SEM CRYSTAL SIZE (MICRONS) | ACID-ITY EQ. (mm/g) | SA ($m^2/g$) | REACT-OR TEMP. (°C.) | ON-STREAM TIME (HRS.) | CONV. (%) | SEL. (%) | YIELD (%) |
| 85 | EX. 14 | 10E | $NH_4^+$/ $TPA^+$ | 11.5 | 6 | 150 | 350 | | | | | | 335 | 20.0 | 93.8 | 32.6 | 30.6 |
| 86 | EX. 15 | 17 | $NH_4^+$/ $TPA^+$ | 11.5 (HBF$_4$) | 6 | 150 | 350 | 357 | 100 | N/A | N/A | N/A | 335 | 12.5 | 100.0 | 13.9 | 13.9 |
| 87 | EX. 15 | 17 | $NH_4^+$/ $TPA^+$ | 11.5 | 6 | 150 | 350 | | | | | | 335 | 38.7 | 99.1 | 16.9 | 16.7 |
| 88 | EX. 15 | 17 | $NH_4^+$/ $TPA^+$ | 11.5 | 6 | 150 | 350 | | | | | | 360 | 41.0 | 100.0 | 16.5 | 16.5 |
| 89 | EX. 15 | 17 | $NH_4^+$/ $TPA^+$ | 11.5 | 6 | 150 | 350 | | | | | | 360 | 113.0 | 91.9 | 30.8 | 28.3 |
| 90 | EX. 16 | 18 | $NH_4^+$/ $TPA^+$ | 11.5 (HF) | 6 | 150 | 350 | 387 | 100 | N/A | N/A | N/A | 335 | 12.5 | 100.0 | 13.8 | 13.8 |
| 91 | EX. 16 | 18 | $NH_4^+$/ $TPA^+$ | 11.5 | 6 | 150 | 350 | | | | | | 335 | 39.0 | 100.0 | 15.6 | 15.6 |
| 92 | EX. 16 | 18 | $NH_4^+$/ $TPA^+$ | 11.5 | 6 | 150 | 350 | | | | | | 360 | 41.0 | 100.0 | 16.8 | 16.8 |
| 93 | EX. 16 | 18 | $NH_4^+$/ $TPA^+$ | 11.5 | 6 | 150 | 350 | | | | | | 360 | 74.5 | 100.0 | 19.6 | 19.6 |

(S) - STIRRED
(M/T) - METHANOL/TOLUENE FEED
N/A - NOT AVAILABLE
$TPA^+$ - TETRAPROPYLAMMONIUM

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for converting an oxygenated hydrocarbon feed as hereinafter defined to a hydrocarbon mixture rich in olefins which comprises contacting, under conversion conditions at a conversion reaction temperature of from about 250° to about 500° C., a feed comprising one or more monohydric alcohols and ethers, with a crystalline alumino-silicate zeolite, said zeolite being prepared by the process comprising:
   (A) admixing to form a reaction mixture substantially free of alkali metal cations:
      (a) at least one tetraalkyl ammonium cation containing compound;
      (b) at least one base in an amount sufficient to impart a pH to the reaction mixture in the initial absence of said acid of (f) of not less than 13 when measured at room temperature;
      (c) at least one silica source;
      (d) at least one alumina source;
      (e) water and
      (f) at least one acid
      in a manner and under conditions sufficient to impart a $SiO_2/Al_2O_3$ mole ratio of about 70 to about 2000 to the crystalline zeolite; the reaction mixture prior to acid addition having a composition within the following molar ratio ranges:
      $(TAA)_2O/SiO_2$, 0.01 to 5
      $SiO_2/Al_2O_3$, 80 to 2200
      $OH^-/SiO_2$, 0.02 to 10
      $H_2O/OH^-$, 5 to 500
      wherein TAA is the sum of the tetraalkyl ammonium cations; the initial pH of the reaction mixture, when measured at room temperature, being adjusted with said acid to be from about 9.0 to about 12.5;
   (B) heating the reaction mixture until crystals of said zeolite form;
   (C) separating said crystals from the reaction mixture; and
   (D) calcining said zeolite.

2. The process of claim 1 wherein in said zeolite preparative procedure said tetraalkylammonium cation containing compound and said base is a tetraalkylammonium hydroxide.

3. The process of claim 2 wherein in said zeolite preparative procedure said tetraalkylammonium hydroxide is tetrapropylammonium hydroxide, the silica source is colloidal silica, the aluminum source is aluminum nitrate, and the acid is selected from the group consisting of $HNO_3$, $HBF_4$, HF, $H_3PO_4$, and $H_3BO_3$.

4. The process of claim 1 wherein in said zeolite preparative procedure the base in said reaction mixture comprises ammonium hydroxide.

5. The process of any one of claims 1 to 4 wherein the feed comprises at least one monohydric alcohol and additionally comprises at least one aromatic compound sufficient to increase the selectivity of the conversion reaction of said methanol to olefins relative to the absence of said aromatic compound.

6. The process of claim 5 wherein the feed further comprises steam in an amount sufficient to increase the conversion of said reaction relative to the absence of steam.

7. A process for converting an oxygenated hydrocarbon feed to a hydrocarbon mixture rich in olefins which comprises contacting, under conversion conditions at a conversion reaction temperature of from about 300° to about 450° C., a feed comprising one or more monohydric alcohols having from about 1 to about 4 carbon atoms, ethers derived therefrom, or mixtures of said alcohols and ethers, with a crystalline aluminosilcate ZSM-5 zeolite, said zeolite being prepared by the process comprising:
   (1) providing a reaction mixture substantially free of alkali metal cations and comprising tetrapropylammonium hydroxide, a silica source, an alumina source and water, said reaction mixture components being present in amounts sufficient to impart;
      (i) an initial pH to the reaction mixture of not less than about 13; (ii) a $SiO_2/Al_2O_3$ mole ratio to the crystalline zeolite of from about 100 to about 1000; and (iii) a composition to the reaction mixture expressed in terms of mole ratios comprising:
      $(TPA)_2O/SiO_2$, 0.5 to 1
      $SiO_2/Al_2O_3$, 110 to 1100
      $H_2O/SiO_2$, 20 to 140
      $OH^-/SiO_2$, 0.2 to 5
      $H_2O/OH^-$, 10 to 200
      wherein TPA signifies tetrapropylammonium;
   (2) adjusting the initial pH of the reaction mixture to between about 11 and about 11.7, when measured at room temperature, by the addition of acid;
   (3) heating the pH adjusted reaction mixture in a manner and under conditions sufficient to cause crystals of said zeolite to form;
   (4) separating said crystals from the reaction mixture; and
   (5) calcining said zeolite.

8. The process of claim 7 wherein the hydrocarbon feed comprises methanol.

9. The process of claim 7 wherein the hydrocarbon feed comprises dimethylether.

10. The process of claim 9 wherein the hydrocarbon feed contains steam in an amount sufficient to provide a mole ratio of dimethylether to steam therein of from about 1:5 to about 1:0.2.

11. The process of claim 8 wherein the feed additionally comprises at least one aromatic compound selected from the group consisting of benzene, toluene, and para-xylene.

12. The process of claim 11, wherein said feed further comprises steam in an amount sufficient to achieve a methanol to water mole ratio of from about 1:0.05 to about 1:0.7.

* * * * *